US010954269B2

(12) United States Patent
Soeberdt et al.

(10) Patent No.: US 10,954,269 B2
(45) Date of Patent: Mar. 23, 2021

(54) ANTI-INFLAMMATORY TRIPEPTIDES

(71) Applicant: Dr. August Wolff Gmbh & Co. KG Arzneimittel, Bielefeld (DE)

(72) Inventors: Michael Soeberdt, Bielefeld (DE); Ulrich Knie, Bad Salzuflen (DE); Christoph Abels, Bielefeld (DE)

(73) Assignee: Dr. August Wolff GmbH & Co. KG Arzneimittel, Bielefeld (DE)

( * ) Notice: Subject to any disclaimer, the term of this patent is extended or adjusted under 35 U.S.C. 154(b) by 0 days.

(21) Appl. No.: 16/249,275

(22) Filed: Jan. 16, 2019

(65) Prior Publication Data

US 2019/0153029 A1    May 23, 2019

Related U.S. Application Data

(62) Division of application No. 15/023,886, filed as application No. PCT/EP2014/070201 on Sep. 23, 2014, now Pat. No. 10,227,379.

(30) Foreign Application Priority Data

Sep. 23, 2013    (EP) .................................... 13185543

(51) Int. Cl.
| | |
|---|---|
| *C07K 5/087* | (2006.01) |
| *A61K 38/00* | (2006.01) |
| *C07K 5/09* | (2006.01) |
| *C07K 5/12* | (2006.01) |
| *C07K 5/083* | (2006.01) |

(52) U.S. Cl.
CPC .......... *C07K 5/0815* (2013.01); *C07K 5/0808* (2013.01); *C07K 5/0812* (2013.01); *C07K 5/123* (2013.01); *A61K 38/00* (2013.01)

(58) Field of Classification Search
CPC .................................... C07K 5/08; C07K 5/00
See application file for complete search history.

(56) References Cited

U.S. PATENT DOCUMENTS

| | | | | |
|---|---|---|---|---|
| 5,389,615 | A | * | 2/1995 | Ferreira ................ C07K 5/0815 514/18.3 |
| 5,718,882 | A | * | 2/1998 | Zamora .................. A61K 49/14 424/1.11 |
| 2003/0119750 | A1 | | 6/2003 | Demuth et al. |

FOREIGN PATENT DOCUMENTS

| | | |
|---|---|---|
| EP | 2110380 A1 | 10/2009 |
| WO | WO-1988/000833 | 2/1988 |
| WO | WO-2002/64131 A2 | 8/2002 |
| WO | WO-2002/094856 | 11/2002 |

OTHER PUBLICATIONS

Brzoska et al. "a-Melanocyte-Stimulating Hormone and Related Tripeptides: Biochemistry, Antiinflammatory and Protective Effects in Vitro and in Vivo, and Furture Perspectives for the Treatment of Immune-Mediated Inflammatory Diseases", Endocrine Reviews, 2007; pp. 581-602 (Year: 2007).*
Gentilucci et al. "Chemical Modifications Designed to Improve Peptide Stability: Incorporation of Non-Natural Amino Acids, Pseudo-Peptide Bonds, and Cyclization", Current Pharmaceutical Design, 2010, pp. 3185-3203 (Year: 2010).*
Chatterjee et al. "N-Methylation of Peptides: A New Perspective in Medicinal Chemistry", Accounts of Chemical Researchh, 2008, pp. 1331-1342 (Year: 2008).*
The National Center for Biotechnology Information "6-Amino-2-(dimethylamino)hexanoic acid" (2007) p. 1 (Year: 2007).*
The National Center for Biotechnology Information "N-Methyl-L-valine" (2005) p. 1 (Year: 2005).*
The National Center for Biotechnology Information "N-Methyl-L-threonine" (2006) p. 1 (Year: 2006).*
Grip et al. "Use of atorvastatin as an anti-inflammatory treatment in Chron's Disease", British Journal of Pharmacology, 2008, pp. 1085-1092 (Year: 2008).*
Urnov, "Methylation and the Genome: the Power of a Small Amendment", The Journal of Nutrition, vol. 132, Issue 8, Aug. 2002, pp. 2450S-2456S (Year: 2002).*
Akagawa, K. et al., Asymmetric Michael Addition of Boronic Acids to a γ-Hydroxy-α,β- Unsaturated Aldehyde Catalyzed by Resin-Supported Peptide, *Organic and Biomolecular Chemistry*, 10(25): 4839-43, May 29, 2012.
Brady, S. et al., Amide and Aspire-Keto Carbonyl Inhibitors of Thrombin Based on Arginine and Lysine: Synthesis, Stability and Biological Characterization, *Bioorganic and Medicinal Chemistry*, 3(8): 1063-1078, Aug. 1995.
Chang, K. et al., Potent Morphiceptin Analogs: Structure Activity Relationships and Morphine-Like Activities, *Journal of Pharmacology and Experimental Therapeutics*, 227(2): 403-408, Nov. 1983.
Salvadori, S. et al., Opioid Peptides, *International Journal of Peptide and Protein Research*, 33(2): 94-102, Feb. 1989.
Goodwin, D, Simerska P., Toth, I; Peptides as Therapeutics with Enhanced Bioactivity, Current Medicinal Chemistry 2012, 19, 4451-4461. Sep. 1, 2012, 11 Pages.
Gentilucci, Luca, De Marco, Rossella, Cerisoli, Lucia, Chemical Modifications Designed to Improve Peptide Stability: Incorporation of Non-Natural Amino Acids, Pseudo-Peptide Bonds, and Cyclization, Current Pharmaceutical Design, 2010, 16, 3185-3203, Jul. 9, 2010, 19 pages.

(Continued)

*Primary Examiner* — Lianko G Garyu
(74) *Attorney, Agent, or Firm* — Julie K. Staple; Dinsmore & Shohl LLP

(57) ABSTRACT

The present invention relates to tripeptide compounds according to the general formula (1) and their use as a medicament, in particular as anti-inflammatory agents.

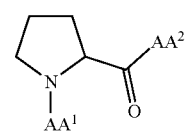

(1)

10 Claims, 6 Drawing Sheets

(56) References Cited

OTHER PUBLICATIONS

Singapore Written Opinion from related patent application No. 11201602161X, dated Mar. 3, 2017.
Aurelio, L. et al., Synthetic Preparation of N-Methyl-a-amino Acid, *Chem. Rev.*, 104: 5823-5846, 2004.
Tiruppathi, C. et al., Kinetic Evidence for a Common Transporter for Glycylsarcosine and Phenylalanylprolylainine in Renal Brush-border Membrane Vesicles, *The Journal of Biological Chemistry*, 265(25): 14870-14874, Sep. 5, 1990.
Toniolo, C. et al., Structure of Peptides from a-Amino Acids Methylated at the a-Carbon, *Biopolymers*, 33: 1061-1072, 1993.
Bajusz et al., Highly Active and Selective Anticoagulants: D-Phe-Pro-Arg-H, a Free Tripeptide Aldehyde Prone to Spontaneous Inactivation, and Its Stable N-Methyl Derivative, D-MePhe-Pro-Arg-H, J Med Chem, pp. 1729-1735, 1990.
Xiao-Li et al., Synthesis and Structure Analysis of a Tripeptide Containing N-methyl Group Amino Acid, Chinese J. Struct., pp. 718-724, 2016.
Banerjee, R. et al., Aib-based peptide backbone as scaffolds for helical peptide mimics, J. Peptide Res., 60: 88-94, 2002.
Jeremic, et al., Synthesis of Cyclohexapepides Containing OPro and Aib Residues, Helvetica Chimica Acta, pp. 3056-3079, 2004.

\* cited by examiner

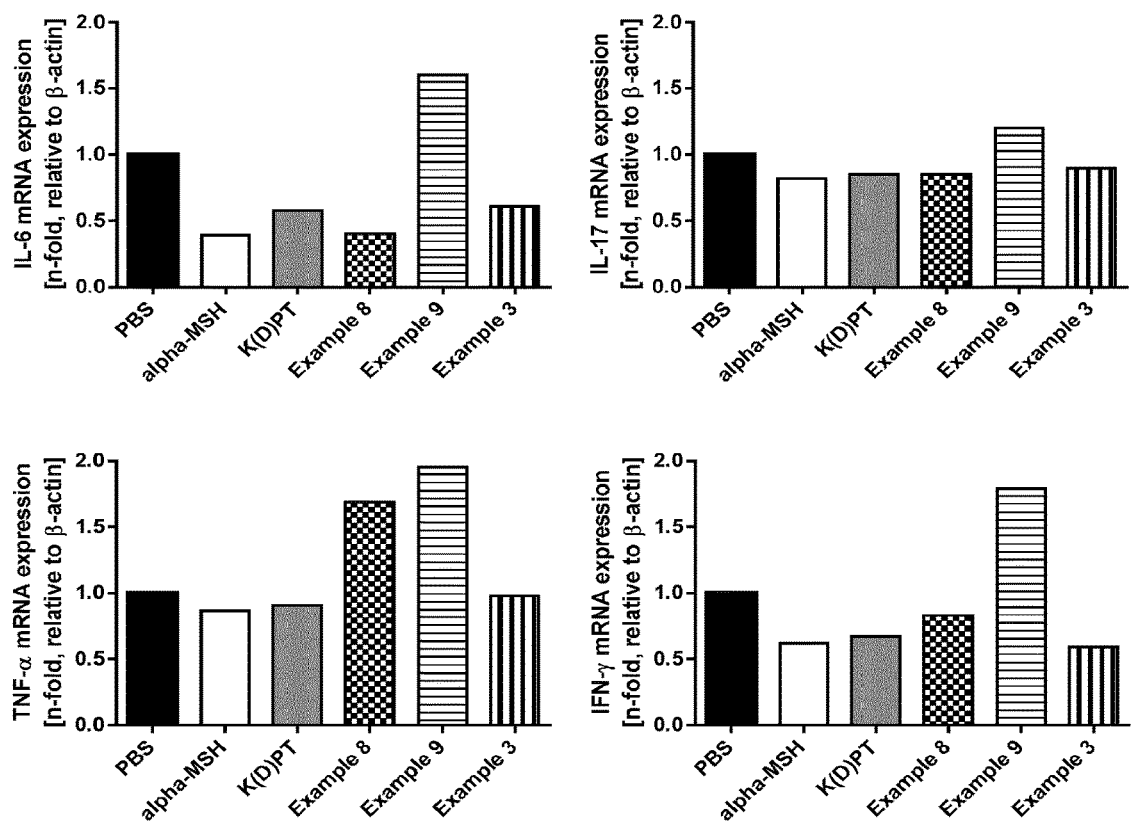
Figure 1: Gene expression analysis: Primary human T cells

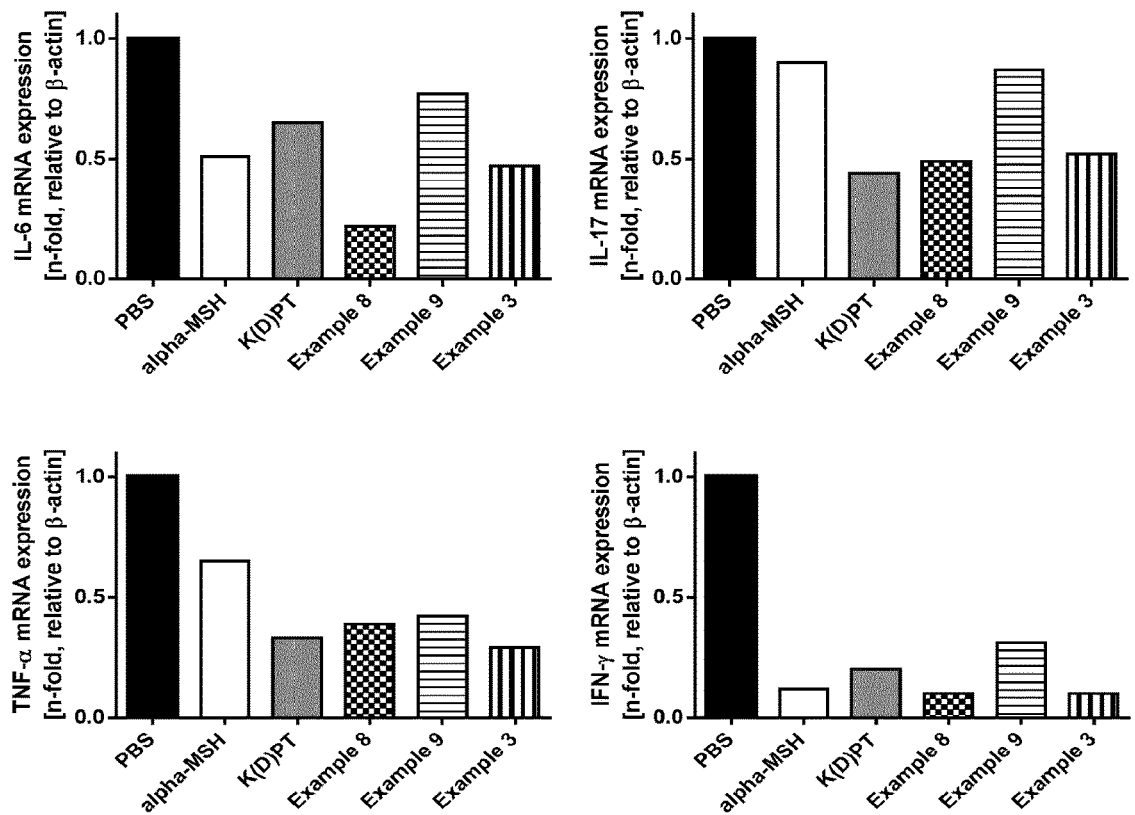
Figure 2: Gene expression analysis: HaCaT

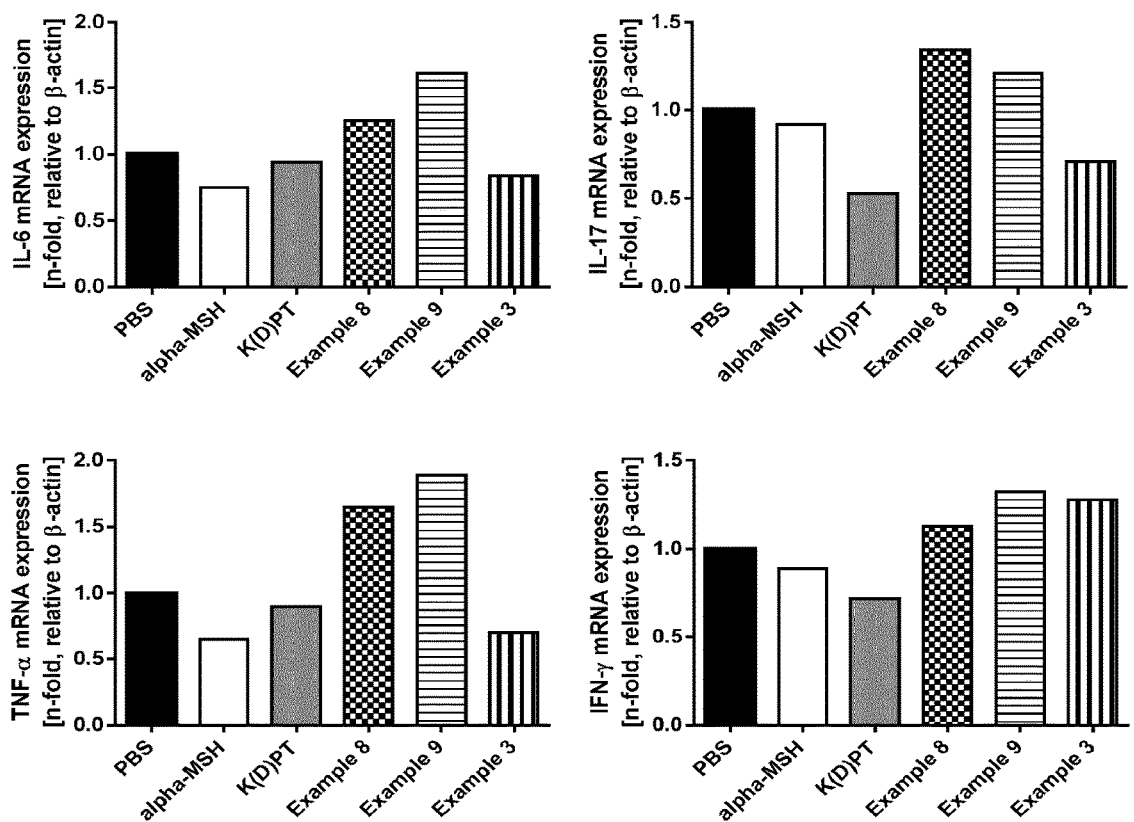
Figure 3: Gene expression analysis: Primary murine T cells

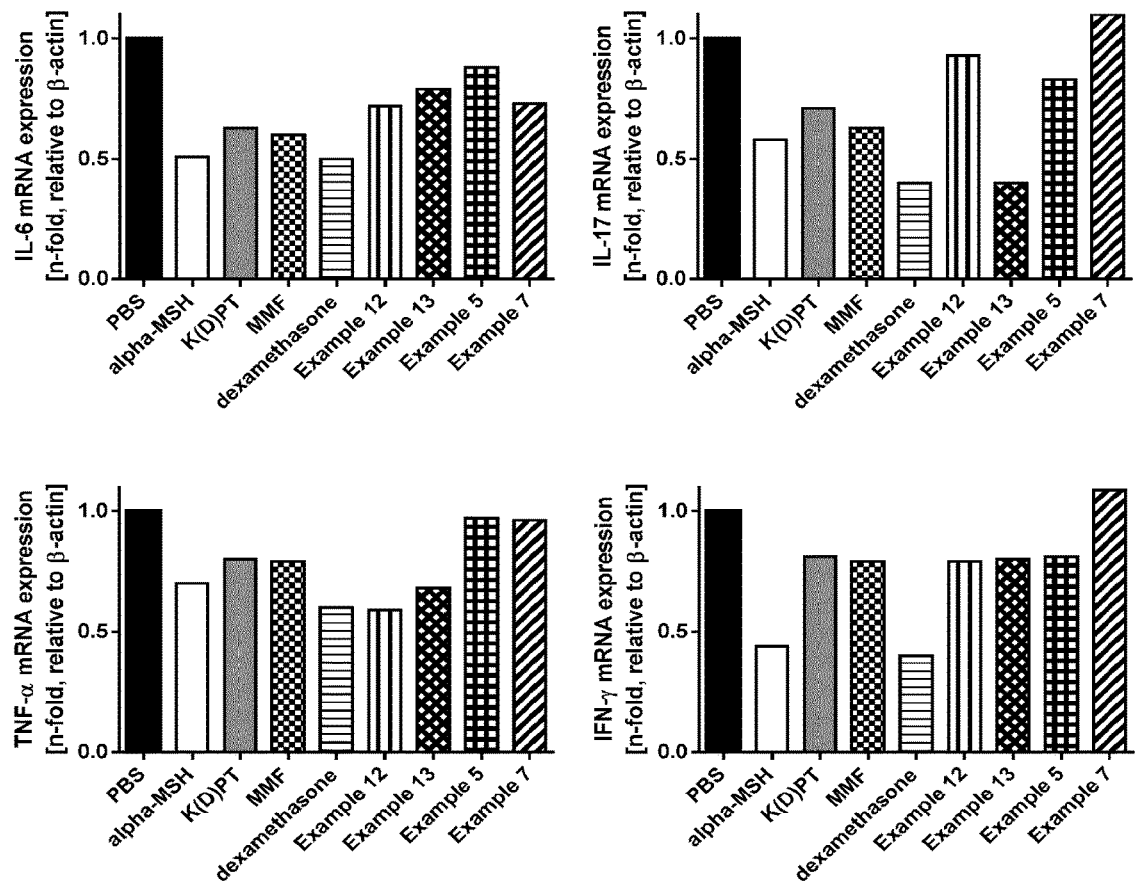
Figure 4: Gene expression analysis: Primary human T cells

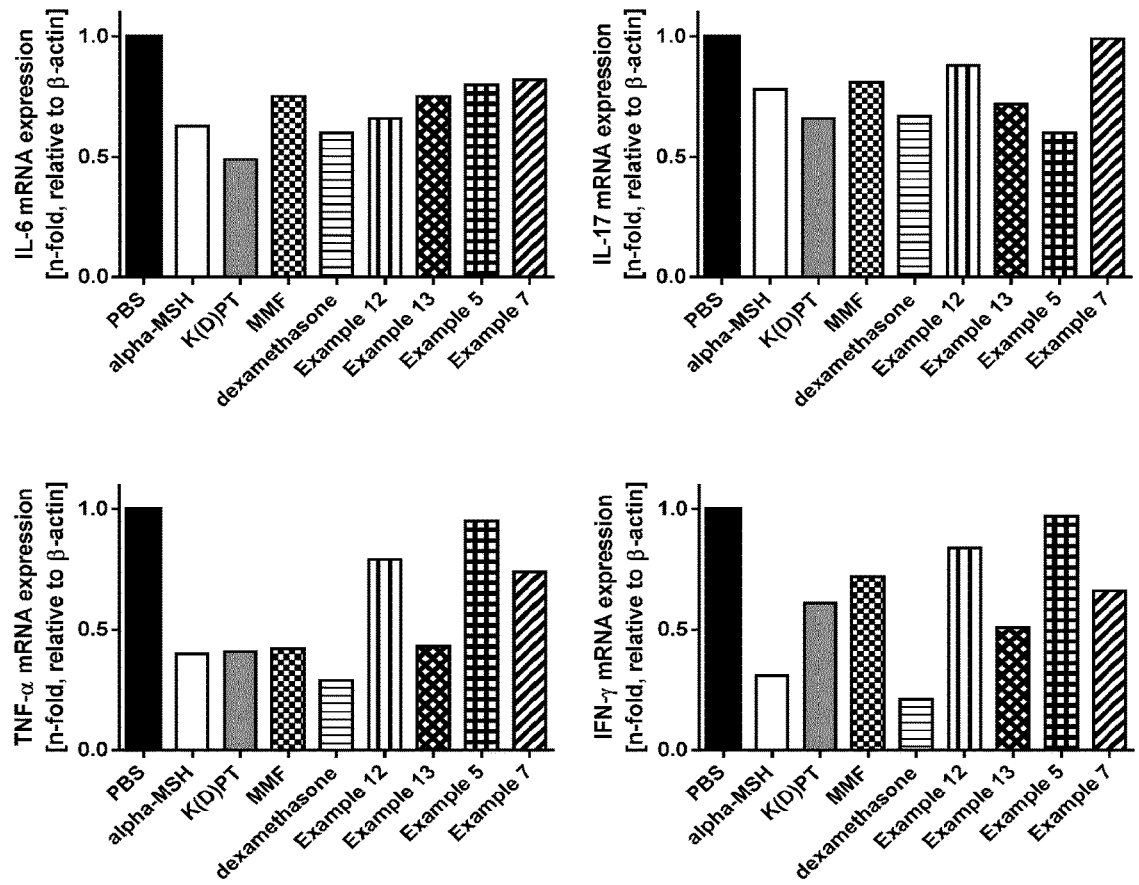
Figure 5: Gene expression analysis: HaCaT

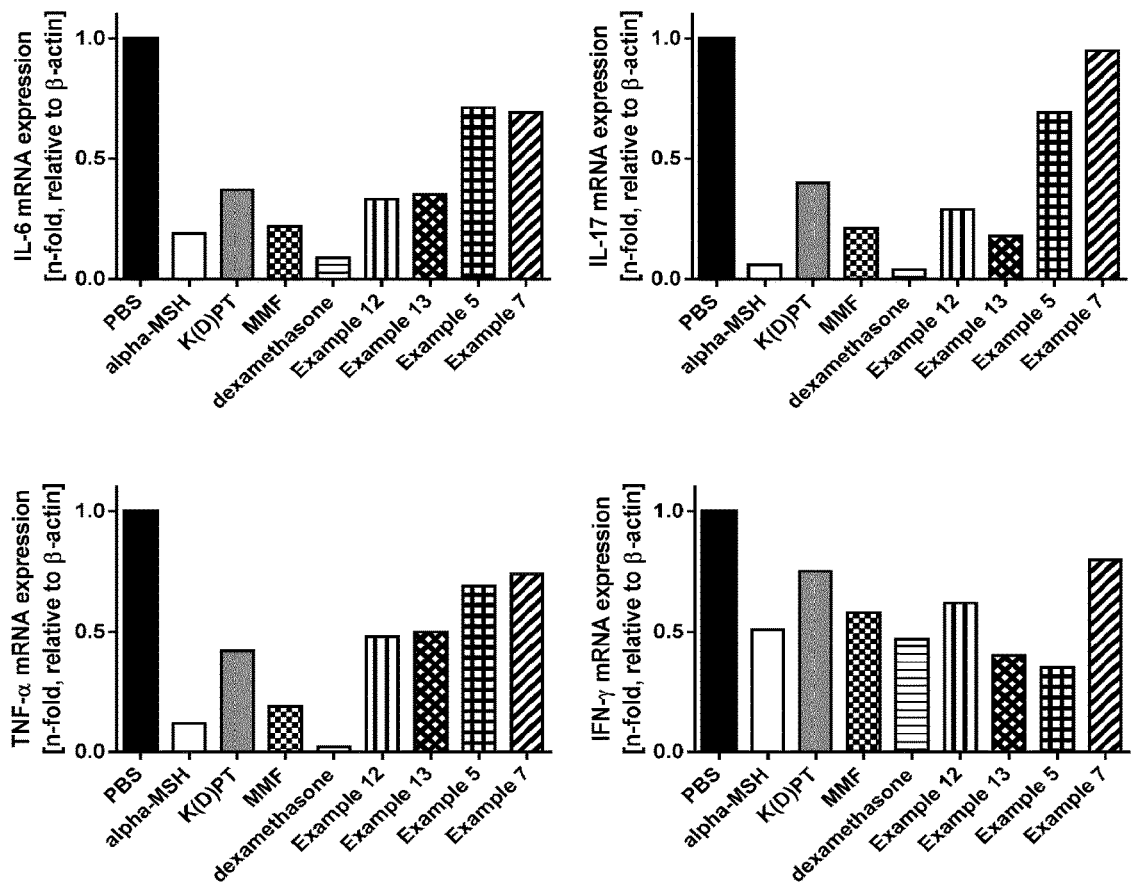
Figure 6: Gene expression analysis: Murine T cells

ANTI-INFLAMMATORY TRIPEPTIDES

REFERENCE TO RELATED APPLICATIONS

This application is a divisional of U.S. patent application Ser. No. 15/023,886, filed Mar. 22, 2016, which is a U.S. national stage application of PCT/EP2014/070201, filed Sep. 23, 2014, which claims priority from EP13185543.9, filed Sep. 23, 2013 The entire content of each application is incorporated herein by reference.

The present invention relates to tripeptide compounds and their use as a medicament, in particular as anti-inflammatory agents.

Treatment of inflammation is of great importance in medicine. Existing treatments, however, are insufficient or problematic. Transient inflammation is a beneficial mechanism that protects mammals from invading pathogens. Uncontrolled inflammation caused by either innate or adaptive immune responses, however, may lead to tissue damage and pain and is the underlying cause of many illnesses, including asthma, as well as other allergic, infectious, autoimmune, degenerative, and idiopathic diseases. Existing treatments often exhibit low, delayed or only temporary efficacy, undesirable side-effects and/or a lack of selectivity.

In view of the large number of types of inflammation and diseases associated with inflammation and the shortcomings of currently available drugs, there is a great need for new active agents to effectively treat these diseases and their symptoms without immunosuppressive adverse effects.

WO88/00833 discloses the use of the tripeptide Lys-Pro-Val for the preparation of a medicament for treating inflammation.

WO02/064131 describes inflammation inhibiting compounds like Lys-Pro-Thr.

WO02/094856 relates to analoges and peptidomimetics of glycyl-L-prolyl-L-glutamic acid (GPE)

WO03/002593 discloses dipeptidyl peptidase IV (DPP IV) inhibitors.

WO2007/080194 describes the use of tripeptidyl peptidase II (TPP II) inhibitors for enhancing the efficacy of gamma-irradiation cancer therapy.

WO2007/088099 discloses the use of TPP II inhibitors in the treatment of ischemia and neurodegeneration.

WO2009/000296 describes the use of TPP II inhibitors in the treatment of autoimmune and inflammatory diseases and transplant rejection.

WO2009/000297 discloses the use of TPP II inhibitors for use in combination with chemotherapy for the treatment of cancer.

WO2012/102832 describes the treatment of autism spectrum disorders using glycly-L-2-methylprolyl-L-glutamic acid.

The invention was based on the object to provide novel compounds which can be used as pharmaceutical active compounds, in particular for combating inflammation. Another object of the present invention is the provision of such compounds with increased stability and improved bioavailability being at the same time safe and secure for the patients.

These objects are achieved by the provision of tripeptides compounds (hereinafter also "compounds") according to the general formula (I) as shown below or a solvate or hydrate thereof or a pharmaceutically acceptable salt thereof:

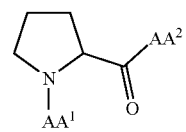

(1)

wherein:

AA$^1$ is selected from ax-amino acids, N$^\alpha$-methyl amino acids and N$^\alpha$,N$^\alpha$-dimethyl amino acids; and AA$^2$ is selected from α-aminoisobutyric acid (Aib), t-butyl glycine, α-aminoisobutyric acid amide, t-butyl glycine amide, N$^\alpha$-methyl amino acids and N$^\alpha$-methyl amino acid amides.

It has surprisingly been found out that these novel compounds of the invention can effectively be used as pharmaceutical active compounds in medicaments, in particular for treating inflammatory diseases, while they at the same time have an increased stability and improved bioavailability as compared to the compounds known in the prior art. Moreover, they are free of undesirable side-effects and are safe for the patients by showing no toxicity.

According to the present invention, the term "amide" includes —C(O)NH$_2$, —C(O)NHR and —C(O)NR$_2$ wherein R is C$_1$-C$_6$ alkyl. Preferably the term amide means —C(O)NH$_2$.

Further, according to the present invention, the term C$_1$-C$_6$ alkyl comprises methyl, ethyl, and i-propyl, n- and i-butyl, n- and i-pentyl and n- and i-hexyl. C$_6$-C$_{10}$ aryl comprises any aromatic C$_6$-C$_{10}$ ring. Preferably it is phenyl. Halogen preferably comprises Cl, Br and I.

Moreover, according to the invention the following definitions are used:

1-Nal 1-naphtylalanine
2-Nal 2-naphtylalanine
Abu α-aminobutyric acid
Aib α-aminoisobutyric acid
Ala alanine
Arg arginine
Asn asparagine
Asp aspartic acid
Cha cyclohexylalanine
Cit citrulline
Cys cysteine
Dab α,γ-diaminobutyric acid
Dap α,β-diaminopropionic acid
Gly glycine
His histidine
Hle homoleucine
Homophe homophenylalanine
Ile isoleucine
Leu leucine
Lys lysine
Met methionine
Nle norleucine
Nva norvaline
Orn ornithine
Phe phenylalanine
Phg phenylglycine
Pro proline
Sar sarcosine
Ser serine
t-butyl-Gly tert.-butylglycine
Tic 1,2,3,4-tetrahydroisoquinoline-3-carboxylic acid
Thr threonine
Trp tryptophan Tyr tyrosine
Val valine Preferred according to the invention are the tripeptide compounds according to general formula (1) as mentioned above, wherein (1) $A^1$ is selected from α-amino acids, $N^α$-methyl amino acids and $N^α,N^α$-dimethyl amino acids; and $AA^2$ is selected from α-aminoisobutyric acid, t-butyl glycine, α-aminoisobutyric acid amide and t-butyl glycine amide, or alternatively, wherein (2) $AA^1$ is selected from α-amino acids, $N^α$-methyl amino acids and $N^α,N^α$-dimethyl amino acids; and $AA^2$ is selected from $N^α$-methyl amino acids and $N^α$-methyl amino acid amides.

More preferred according to the invention are the tripeptide compounds (hereinafter also "compounds") according to general formula (2):

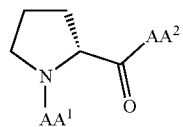

(2)

wherein $AA^1$ is selected from α-amino acids, $N^α$-methyl amino acids and $N^α,N^α$-dimethyl amino acids; and $AA^2$ is selected from $N^α$-methyl amino acids and $N^α$-methyl amino acid amides.

These compounds provide for a further improved efficacy, particularly in treating inflammatory diseases, and increased stability and bioavailability.

According to a further preferred embodiment of the invention, in the tripeptide compounds of general formula (1) and/or general formula (2), $AA^1$ is an $N^α,N^α$-dimethyl amino acid and $AA^2$ is an $N^α$-methyl amino acid, respectively.

$N^α$-methyl amino acids and $N^α,N^α$-dimethyl amino acids in the definition of $AA^1$ according to the invention are preferably selected from the group consisting of $N^α$-methyl-1-Nal, $N^α,N^α$-dimethyl-1-Nal, $N^α$-methyl-2-Nal, $N^α,N^α$-methyl-Abu, $N^α,N^α$-dimethyl-Abu, $N^α$-methyl-Ala, $N^α,N^α$-dimethyl-Ala, $N^α$-methyl-Arg, $N^α,N^α$-dimethyl-Arg, $N^α$-methyl-Asn, $N^α,N^α$-dimethyl-Asn, $N^α$-methyl-Cha, $N^α,N^α$-dimethyl-Cha, $N^α$-methyl-Cit, $N^α,N^α$-dimethyl-Cit, $N^α$-methyl-Cys, $N^α,N^α$-dimethyl-Cys, $N^α$-methyl-Dab, $N^α,N^α$-dimethyl-Dab, $N^α$-methyl-Dap, $N^α,N^α$-dimethyl-Dap, Sar, $N^α,N^α$-dimethyl-Gly, $N^α$-methyl-His, $N^α,N^α$-dimethyl-His, $N^α$-methyl-Hle, $N^α,N^α$-dimethyl-Hle, $N^α$-methyl-Homophe, $N^α,N^α$-dimethyl-Homophe, $N^α$-methyl-Ile, $N^α,N^α$-dimethyl-Ile, $N^α$-methyl-Leu, $N^α,N^α$-dimethyl-Leu, $N^α$-methyl-Lys, $N^α,N^α$-dimethyl-Lys, $N^α$-methyl-Met, $N^α,N^α$-dimethyl-Met, $N^α$-methyl-Nle, $N^α,N^α$-dimethyl-Nle, $N^α$-methyl-Nva, $N^α,N^α$-dimethyl-Nva, $N^α$-methyl-Orn, $N^α,N^α$-dimethyl-Orn, $N^α$-methyl-Phe, $N^α,N^α$-dimethyl-Phe, $N^α$-methyl-Phg, $N^α,N^α$-dimethyl-Phg, $N^α$-methyl-Ser, $N^α,N^α$-dimethyl-Ser, $N^α$-methyl-t-butyl-Gly, $N^α,N^α$-dimethyl-t-butyl-Gly, $N^α$-methyl-Tic, $N^α$-methyl-Thr, $N^α,N^α$-dimethyl-Thr, $N^α$-methyl-Trp, $N^α,N^α$-dimethyl-Trp, $N^α$-methyl-Tyr, $N^α,N^α$-dimethyl-Tyr, $N^α$-methyl-Val $N^α,N^α$-dimethyl-Val, $N^α$-methyl-2-thienylalanine, $N^α,N^α$-dimethyl-2-thienalanine, $N^α$-methyl-3-benzothienylalanine, $N^α,N^α$-dimethyl-3-benzothienylalanine, $N^α$-methyl-2-pyridylalanine, $N^α,N^α$-dimethyl-2-pyridylalanine, $N^α$-methyl-3-pyridylalanine and $N^α,N^α$-dimethyl-3-pyridylalanine, Phe may be substituted by one or more substituents selected from the group of —$NH_2$, —$NH(C_1$-$C_6alkyl)$, —$N(C_1$-$C_6alkyl)_2$, —$CH_2NH_2$, —$CH_2NH(C_1$-$C_6alkyl)$, —$CH_2N(C_1$-$C_6alkyl)_2$, OH, halogen, —CN, $CF_3$, —$NHC(O)CH_3$, —$C(O)CH_3$, —$OC_1$-$C_6alkyl$, —$C(O)NH_2$ and —$C_1$-$C_6alkyl$.

$N^α$-methyl amino acids and $N^α$-methyl amino acid amides in the definition of $AA^2$ according to the invention are preferably selected from the group consisting of $N^α$-methyl-Abu-OH, $N^α$-methyl-Ala-OH, Sar-OH, $N^α$-methyl-Hle-OH, $N^α$-methyl-Ile-OH, $N^α$-methyl-Leu-OH, $N^α$-methyl-Nle-OH, $N^α$-methyl-Nva-OH, $N^α$-methyl-Ser-OH, $N^α$-methyl-t-butyl-Gly-OH, $N^α$-methyl-Thr-OH, $N^α$-methyl-Val-OH, $N^α$-methyl-Abu-$NH_2$, $N^α$-methyl-Ala-$NH_2$, Sar-$NH_2$, $N^α$-methyl-Hle-$NH_2$, $N^α$-methyl-Ile-$NH_2$, $N^α$-methyl-Leu-$NH_2$, $N^α$-methyl-Nle-$NH_2$, $N^α$-methyl-Nva-$NH_2$, $N^α$-methyl-Ser-$NH_2$, $N^α$-methyl-t-butyl-Gly-$NH_2$, $N^α$-methyl-Thr-$NH_2$ and $N^α$-methyl-Val-$NH_2$.

α-Amino acids according to the invention comprise all amino acids having the amino group in α-position to the carboxylic acid group. Preferably, in the definition of $AA^1$ according to the invention the α-amino acids are selected from the group consisting of 1-Nal, 2-Nal, Abu, Ala, Arg, Asn, Cha, Cit, Cys, Dab, Dap, Gly, His, Hle, Homophe, Ile, Leu, Lys, Met, Nle, Nva, Orn, Phe, Phg, Ser, t-butyl-Gly, Tic, Thr, Trp, Tyr, Val, 2-thienylalanine, 3-benzothienylalanine, 2-pyridylalanine and 3-pyridylalanine. Phe may be substituted by one or more substituents selected from the group of —$NH_2$, —$NH(C_1$-$C_6alkyl)$, —$N(C_1$-$C_6alkyl)_2$, —$CH_2NH_2$, —$CH_2NH(C_1$-$C_6alkyl)$, —$CH_2N(C_1$-$C_6 alkyl)_2$, OH, halogen, —CN, $CF_3$, —$NHC(O)CH_3$, —$C(O)CH_3$, —$OC_1$-$C_6alkyl$, —$C(O)NH_2$ and —$C_1$-$C_6alkyl$, $AA^1$ is more preferably selected from Lys, Orn, Nle and Phe.

Preferred tripeptide compounds according to the present invention are those, wherein in general formula (1) $AA^1$ is selected from Lys, Orn, Nle, Phe, $N^α$-methyl-Phe, $N^α,N^α$-dimethyl-Nle, and $N^α,N^α$-dimethyl-Phe and $AA^2$ is α-aminoisobutyric acid, t-butyl glycine, and α-aminoisobutyric acid amide.

Particularly preferred tripeptide compounds according to the present invention are selected from the group consisting of H-(L)-Lys-(D)-Pro-Aib-OH, H-(L)-Lys-(D)-Pro-$N^α$-methyl-(L)-Thr-OH, H-(L)-Lys-(L)-Pro-Aib-OH, H-(L)-Lys-(L)-Pro-(L)-t-butyl-Gly-OH, $N^α,N^α$-dimethyl-(L)-Lys-(D)-Pro-$N^α$-methyl-(L)-Thr-OH, H-(L)-Lys-(L)-Pro-Alb-$NH_2$, H-(L)-Orn-(L)-Pro-Aib-OH, H-(L)-Nle-(L)-Pro-Aib-OH, H-(L)-Phe-(L)-Pro-Aib-OH, $N^α,N^α$-dimethyl-(L)-Lys-(D)-Pro-$N^α$-methyl-(L)-Thr-$NH_2$, $N^α,N^α$-dimethyl-(L)-Lys-(D)-Pro-$N^α$-methyl-(L)-Val-OH, $N^α,N^α$-dimethyl-(L)-Nle-(D)-Pro-$N^α$-methyl-(L)-Thr-OH, $N^α$-methyl-(D)-Phe-(L)-Pro-Aib-OH, H-(D)-Phe-(L)-Pro-Aib-OH, $N^α,N^α$-dimethyl-(L)-Phe-(t)-Pro-Aib-OH, $N^α,N^α$-dimethyl-(L)-Nle-(L)-Pro-Aib-OH, or $N^α,N^α$-dimethyl-(L)-Phe-(D)-Pro-$N^α$-methyl-(L)-Thr-OH, or a solvate or hydrate thereof, or a pharmaceutically acceptable salt thereof.

The compounds according, to the invention can furthermore be used in the form of their acids or their bases or in the form of their salts, in particular the physiologically acceptable salts, or in the form of their solvates, in particular their hydrates.

The pharmaceutically acceptable salts can be base addition salts. These include salts of the compounds according to the invention with inorganic bases, such as alkali metal hydroxides, alkaline earth metal hydroxides, or with organic bases, such as mono-, di- or triethanolamine.

Acid addition salts, in particular with inorganic acids, such as hydrochloric acid, sulfuric acid or phosphoric acid, or with suitable organic carboxylic or sulfonic acids, or with amino acids, can further advantageously be used.

Pharmaceutically acceptable salts of the compounds according to the invention are chosen, for example, from the group comprising chlorides, bromides, iodides, hydrochlorides, hydrobromides, sulfonates, methanesulfonates, sulfates, hydrogen sulfates, sulfites, hydrogen sulfites, phosphates, nitrates, methanoates, acetates, proprionates, lactates, citrates, glutarates, maleates, malonates, malates, succinates, tartrates, oxalates, fumarates, benzoates, p-toluenesulfonates and/or salts of amino acids, preferably the proteinogenic amino acids.

The compounds according to the invention are suitable for use as medicaments. They are capable of having an analgesic, antipyretic, antipruritic, antiinflammatory and/or spasmolytic action. According to the invention the compounds and the medicaments containing the compounds are preferably used in a method for the therapeutic and/or prophylactic treatment of diseases chosen from the group comprising acute and chronic inflammatory diseases, acute and chronic pain, pruritus, hyponatremia, edema, ileus, tussis and glaucoma. Further diseases that may be treated according to the invention are MS (multiple sclerosis), Morbus Parkinson and Morbus Alzheimer.

In advantageous embodiments the compounds according to the invention can be used in particular for therapeutic and/or prophylactic treatment, diagnosis and/or therapy of inflammatory diseases.

The invention also provides the use of the compounds according to the invention for the preparation of a medicament for therapeutic and/or prophylactic treatment of inflammatory diseases.

According to the invention pain-related diseases are particularly those diseases involving pain due to inflammatory reactions (also named as inflammatory pain-related diseases and inflammatory pain).

Moreover, according to the invention inflammatory diseases are chosen from the group comprising cardiovascular inflammation, neurological inflammation, skeletal inflammation, skin inflammation, muscular inflammation, gastrointestinal inflammation, ocular inflammation, otic inflammation, inflammation due to insect bites and inflammation due to wound healing; atherosclerosis, ischemia, restenosis and vasculitis; asthma, Sjogren's syndrome, pulmonary inflammation, chronic airway inflammation and chronic obstructive pulmonary disease (COPD), allergy, psoriasis, psoriatic arthritis, eczema, scleroderma, atopic dermatitis and systemic lupus erythematosus arthritis, synovitis, osteomyelitis, rheumatoid arthritis, osteoarthritis and ankylosing spondylitis; septicemia and septic shock, diabetes, glucose intolerance, insulin resistance and obesity, colitis, ulcerative colitis, Crohn's disease, IBD and IBS, and the inflammatory diseases and conditions due to tumor proliferation, tumor metastasis or transplantation rejection (Graft-vs-Host-disease; GvHD).

In particular, inflammatory diseases are chosen from the group comprising inflammatory diseases of the gastrointestinal tract, in particular inflammatory bowel diseases, such as Crohn's disease and/or colitis ulcerosa, acute or chronic inflammatory changes with inflammation of the gall bladder, inflammatory pseudopolyps, colitis cystica profunda, pneumatosis cystoides intestinales, pancreatitis, appendicitis, cardiovascular inflammation due to arthereosclerosis, ischemia, restenosis and/or vasculitis, sepsis, septicemia, allergies, asthma, Sjogren's syndrome, pulmonary inflammation, chronic airway inflammation, chronic obstructive pulmonary disease (COPD), tumor proliferation, tumor metastasis, transplant rejection, inflammatory diseases of the joints, such as rheumatoid arthritis, vulvovaginitis, and/or inflammatory diseases of the brain, skin, hair follicle, urogenital tract and of the eyes, sinusitis, tenosynovitis, bursitis, tendonitis, lateral epicondylitis, adhesive capsulitis, osteomyelitis, osteoarthritic inflammation, ocular inflammation, otitic inflammation and/or autoimmune inflammation, psoriasis, psoriatic arthritis, contact dermatitis, atopic eczema, scleroderma and other fibrotic diseases, systemic lupus crythematous, urticaria, lichen planus, lymphoma and/or allergic diseases or characterized by mast cell involvements.

Pruritus (itching), in particular pruritoceptive pruritus, is a frequent symptom in skin diseases conventionally experienced as a type of pain stimulus. The itching sensation triggers the desire to scratch the affected area. Skin damaged by scratching further offers infectious pathogens a good nutrient medium and inflammations of scratched-open areas of skin are not infrequent. Moreover, itching and scratching itself may elicit an inflammatory reaction. Pruritic skin and hair diseases are chosen from the group comprising pruritus, psoriasis, psoriatic arthritis, contact dermatitis, atopic eczema, alopecia areata, scleroderma and other fibrotic diseases, systemic lupus erythematous, urticaria, lichen planus, lymphoma and/or allergic diseases or characterized by mast cell involvements.

The diseases in the sense of the present invention also comprise other diseases such as hyponatremia, edema, ileus, tussis, glaucoma, MS (multiple sclerosis), Morbus Parkinson and Morbus Alzheimer.

The organs involved in the diseases to be treated by the compounds according to the invention are in particular the so-called barrier organs, namely the gastrointestinal tract, skin, lung, urogenital tract; the brain; the ear nose and throat tract; teeth; bones; liver; and hair. Particularly preferred embodiments of the invention relate to the treatment of the diseases of the barrier organs.

Diseases of the gastrointestinal tract are chosen from the group comprising irritable bowel syndrome, gastric lesions, gastrointestinal ulcerations, exogenous and endogenous damage to the gastrointestinal mucosa, malfunctions of the gastrointestinal tract, adenomas, in particular in the intestine, and/or juvenile polyps.

Diseases of the lung (respiratory diseases) include inflammatory lung disease, obstructive lung diseases such as chronic obstructive pulmonary disease (COPD), restrictive lung diseases, respiratory tract infections such as upper respiratory tract infection, lower respiratory tract infection, malignant tumors and benign tumors, pleural cavity diseases, pulmonary vascular diseases, and neonatal diseases.

Diseases of the urogenital tract include analgesic nephropathy, bladder cancer, cystocele (fallen bladder), end stage renal disease (ESRD), glomerulonephritis, glomerulosclerosis, goodpasture syndrome, hematuria (blood in the urine), hemolytic uremic syndrome, immunoglobulin A (IgA) nephropathy, impotence/erectile dysfunction, interstitial cystitis, kidney cancer, kidney stones, kidney transplantation, male factor infertility, nephrotic syndrome, neurogenic bladder, Peyronie's disease, and polycystic kidney disease.

Further diseases that may be treated with the compounds of the present invention are described in US 2011/0212882 A1 being incorporated herein by reference.

Preferably the tripeptides and the medicaments containing the tripeptides are used for the treatment and/or prophylaxis of inflammatory diseases of the skin, of inflammatory diseases of the gastrointestinal tract, of inflammatory diseases of the (blood) vessels, of autoimmune inflammation, allergic reactions and/or transplant rejections.

It is known that peptides in general and even small dipeptides like carnosine exhibit an inherent instability (Goebel, A S B et al., Dermal Peptide Delivery Using Enhancer Molecules and Colloidal Carrier Systems—Part I: Carnosine, Skin Pharmacology & Physiology (2012), 25, 281-287). Moreover, H-Lys-Pro-Val-OH (KPV) is highly instable and degrades easily under formation of a lysine-proline diketopiperazine. A further advantage of the compounds according to the invention results from the fact that no or a reduced degradation is observed in aqueous solution and in the presence of homogenized tissue.

Another advantage of the compounds of the present invention is the decreased hydrophilicity compared to H-Lys-(D)-Pro-Thr-OH (K(D)PT). Thus, the compounds show an improved penetration of biological barriers. Moreover, the compounds of the present invention are safe and secure for the patients. In particular, no toxicity could be observed. Thus, the compounds of the invention show an improved safety profile.

The compounds according to the invention or compositions/medicaments containing these can be administered systemically or topically. Preferably, the compounds or compositions/medicaments according to the invention are administered topically, in particular in the form of creams, ointments, plasters or tinctures.

In the context of the present invention, the term "prophylactic treatment" is understood as meaning in particular that the compounds according to the invention can be administered before symptoms of a disease occur or the risk of a disease exists.

The compounds according to the invention can be administered according to conventional methods, for example orally, dermally, intranasally, transmucosally, pulmonally, enterally, buccally, rectally, intraurethral, aural, by inhalation, by means of injection, for example intravenously, parenterally, intraperitoneally, intradermally, subcutaneously and/or intramuscularly and/or locally, for example on painful areas of the body. Oral administration is particularly preferred.

The compounds according to the invention can be used in particular for the preparation of medicaments by being brought into a suitable dosage form together with at least one carrier substance or auxiliary substance, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules.

Pharmaceutical dosage forms with delayed release (sustained release formulation) are furthermore preferred for oral administration of the compounds according to the invention. Examples of formulations with delayed release are sustained release matrix tablets, multilayered tablets, the coating of which can be, for example, constructed to be resistant to gastric juice, such as coatings based on shellac, sustained release capsules or formulations using biodegradable polymers, for example polylactic acid) polymers.

Conventional physiologically acceptable pharmaceutical auxiliary substances, preferably chosen from the group comprising carrier materials, fillers, solvents, diluents, wetting agents, emulsifiers, dyestuffs, preservatives, disintegrating agents, lubricants, salts for influencing the osmotic pressure, buffer substances, aromas and/or binders, can be used for the preparation of the medicaments.

The compounds of formula (1) and formula (2) according to the present invention may be prepared using general procedures of solid-phase peptide synthesis known to the skilled person. A more detailed description is provided in the Example section below.

Alternatively, the compounds of formula (1) and formula (2) according to the present invention can also be prepared in solution.

BRIEF DESCRIPTION OF THE DRAWINGS

FIG. 1 is a diagram that shows gene expression analysis of pro-inflammatory cytokines in primary human T cells. Cells were activated with PMA/Ionomycin and treated with PBS, α-MSH, K(D)PT and Examples 3, 8 and 9, respectively, at a concentration of $10^{-9}$ M. Values are normalized to β-actin and are shown relative to the gene expression in PBS-stimulated cells.

FIG. 2 is a diagram that shows gene expression analysis of pro-inflammatory cytokines in human keratinocytes (HaCaT). Cells were activated with PMA/Ionomycin and treated with PBS, α-MSH, K(D)PT and Examples 3, 8 and 9, respectively, at a concentration of $10^{-9}$ M. Values are normalized to β-actin and are shown relative to the gene expression in PBS-stimulated cells.

FIG. 3 is a diagram that shows gene expression analysis of pro-inflammatory cytokines in primary murine T cells. Cells were activated with PMA/Ionomycin and treated with PBS, α-MSH, K(D)PT and Examples 3, 8 and 9, respectively, at a concentration of $10^{-9}$ M. Values are normalized to β-actin and are shown relative to the gene expression in PBS-stimulated cells.

FIG. 4 is a diagram that shows gene expression analysis of pro-inflammatory cytokines in primary human T cells. Cells were activated with PMA/Ionomycin and treated with PBS, α-MSH, K(D)PT, mycophenolate mofetil (MMF), dexamethasone and Examples 5, 7, 12 and 13, respectively, at a concentration of $10^{-9}$ M. Values are normalized to β-actin and are shown relative to the gene expression in PBS-stimulated cells.

FIG. 5 is a diagram that shows gene expression analysis of pro-inflammatory cytokines in human keratinocytes (HaCaT). Cells were activated with PMA/Ionomycin and treated with PBS, α-MSH, K(D)PT, mycophenolate mofetil (MMF), dexamethasone and Examples 5, 7, 12 and 13, respectively, at a concentration of $10^{-9}$ M. Values are normalized to β-actin and are shown relative to the gene expression in PBS-stimulated cells.

FIG. 6 is a diagram that shows gene expression analysis of pro-inflammatory cytokines in primary murine T cells. Cells were activated with PMA/Ionomycin and treated with PBS, α-MSH, K(D)PT, mycophenolate mofetil (MMF), dexamethasone and Examples 5, 7, 12 and 13, respectively, at a concentration of $10^{-9}$ M. Values are normalized to β-actin and are shown relative to the gene expression in PBS-stimulated cells.

EXAMPLES

The following describes detailed examples of the invention. Therein, various reagent symbols and abbreviations have the following meanings:
Boc tert-butoxycarbonyl
BTC bis(trichloromethyl) carbonate
DIC N,N'-diisopropylcarbodiimide
DIPEA ethyl-diisopropylamine
DMF N,N-dimethylformamide
DMSO dimethyl sulfoxide
eq. equivalents ESI-MS electrospray mass spectrometry
Fmoc 9-H-fluoren-9-ylmethoxycarbonyl
h hour(s)
HATU 2-(1H-7-azabenzotriazol-1-yl)-1,1,3,3-tetramethyl uronium hexafluoro-phosphate methanaminium
HOBt 1-hydroxybenzotriazole
HOAc acetic acid
HPLC high performance liquid chromatography
m/z mass-to-charge ratio
min minute(s)
MeCN acetonitrile
MeOH methanol
MW molecular weight
RT room temperature
T temperature
tBu tertiary butyl
TFA trifluoroacetic acid
TIS triisopropylsilane
$t_R$ (min) HPLC retention time
Analytical Methods
HPLC Analytical HPLC separations were performed on an Abimed (D-Langenfeld) Gilson HPLC (sample concentration 1 mg/ml in $H_2O$) with an analytical column Reprospher C18-DE (5 µm, 50×4.6 mm) manufactured by Dr. Maisch (D-Ammerbuch). A gradient of water/0.1% trifluoroacetic acid (v/v) (eluent A) and acetonitrile/0.1% trifluoroacetic acid (v/v) (eluent B) with a flow rate of 1 ml/min (10 mm method) was used.

The purity of the products was assigned on the basis of the peak areas determined at λ=214 nm.

ESI-MS

ESI-MS-analysis of fractions was performed on a Waters-Micromass (D-Eschborn) ZQ mass spectrometer.

Synthesis of Peptides, General Procedures

Loading of the Resin

All peptides were prepared by solid-phase peptide synthesis using Fmoc/tBu-strategy using CITCP (Chloro-(2'-chloro)trityl polystyrene resin H100 33, Rapp Polymere, Tübingen, Germany). Peptide amides were synthesized on Rink-amide polystyrene resin (H100 23, Rapp).

CITCP resin (capacity 1.48 mmol/g) was equilibrated with DMF for 10 min and washed with DMF. A solution of 1 eq. of the Fmoc-amino acid (relative to the loading of the resin) and 4 eq. DIPEA in DMF was added to the resin and shaken for 120 minutes. The resin was filtered off and washed with DMF. The resin was capped with 10 eq. of methanol and 5 eq. of DIPEA in DMF and washed with DMF, DCM and diethyl ether.

The Rink resin (capacity 0.67 mmol/g) was deprotected using 30% piperidin in DMF (2×15 min). After washing with DMF a solution of 3 eq. Fmoc-amino acid, 3 eq. TBTU and 6 eq. DIPEA in DMF was added. The mixture was shaken for 180 minutes. The resin was filtered off and washed with DMF, DCM and diethyl ether. The completeness was checked by Ninhydrin assay.

After resin loading, the loading density was estimated via UV absorbance measurement. The absorption of the cleaved Fmoc-dibenzofulven species was detected at 292 nm. The resin loadings for all Fmoc-amino acids were 0.5 mmol/g excluding N-Me-amino acids N-Me-Thr(tBu), tert.-butylglycine and N-Me-Val, which resulted in a substitution of about 0.4 mmol/g.

Procedure for the Couplings

A solution of 30% piperidine in DMF was added to the resin and the mixture was incubated for 5 min. The resin was filtered off, and the procedure was repeated for 15 min. The resin was filtered off and washed with DMF.

Fmoc-amino acids (3 eq.) were dissolved with HOBt (3 eq.) in DMF. Coupling reagents DIC (3 eq.) or TBTU (3 eq.) with DIPEA (6 eq.) and Fmoc-amino acids were added to the resin. After 180 min (DIC) or 120 min (TBTU) coupling time, coupling reagents were filtered off and the resin was washed with DMF, DCM and diethyl ether.

Coupling of Fmoc-Amino Acids Following N-Me-Amino Acids

The resin was washed with dry THF and incubated with DIPEA (14 eq.) in dry THF for 1-2 min. The resin was filtered off. Fmoc-amino acids (3.5 eq.) were dissolved in a solution of BTC in dry THF (68 mM). 2,4,6-Collidine (10 eq.) was added and the suspension was added to the resin. After 180 minutes the resin was filtered off and washed with DCM, THF and DMF. The completeness of the coupling was monitored with the chloranil test.

N-Terminal Coupling of $Me_2$-Amino Acids $Me_2$-amino acids (3 eq.) were dissolved in DMF with HOBt (3 eq.), 3 eq. HATU and DIPEA (6 eq.). The solution was added to the resin and shaken for 2 hours. The resin was filtered off and washed with DMF, DCM and diethyl ether.

Cleavage

The peptides were cleaved off the resin and side-chain deprotected with trifluoroacetic acid/TIS/water (92.5/5/2.5) within 3 hours. The solvent was evaporated in vacuum. The oil was treated with diethyl ether to precipitate and washed twice with diethyl ether. Peptides were dissolved in tert-.butyl alcohol/water (80/20) by sonication and lyophilized.

To exchange the counter ion, the peptides were dissolved in acetic acid (100 mg in 5 ml) and sonificated for 1 hour. The peptides were precipitated with diethyl ether, decanted, dissolved in tert.butyl alcohol by sonication and lyophilized.

All Fmoc-amino acids, standard side chain protecting groups: tBu (Thr) and Boc (Lys, Orn, Dab).

$N^\alpha,N^\alpha$-Dimethyl amino acids can be synthesized as described in Garcia-Lopez, M T et al., Archiv der Pharmazie (1989), 322, 145-152.

The compounds obtained according to the present invention are summarized in Tables 1 and 2 below.

TABLE 1

| No. | AA¹ | AA² | HPLC $t_g$ (min) | MW (calc.) free base | MS [M + H⁺] (found) |
|---|---|---|---|---|---|
| 1 | (lysine) | (aminoisobutyric acid) | 3.91 | 328.41 | 329 |
| 2 | (lysine) | (N-methyl threonine) | 3.48 | 358.44 | 359 |
| 3 | (N,N-dimethyl lysine) | (N-methyl threonine) | 3.97 | 386.50 | 387 |
| 4 | (N-methyl lysine) | (N-methyl threonine) | 3.19 | 385.51 | 386 |
| 5 | (N,N-dimethyl lysine) | (N-methyl valine) | 3.95 | 384.52 | 385 |

TABLE 1-continued

[Structure: pyrrolidine with AA² attached via C=O, and AA¹ attached to N]  x HOAc

| No. | AA¹ | AA² | HPLC t_g (min) | MS MW (calc.) free base | [M + H⁺] (found) |
|---|---|---|---|---|---|
| 6 | [N,N-dimethyl butyl amino acid structure] | [N-methyl threonine structure] | 4.05 | 371.48 | 372 |
| 7 | [N,N-dimethyl phenylalanine structure] | [N-methyl threonine structure] | 4.11 | 405.50 | 406 |

TABLE 2

[Structure: pyrrolidine with AA² attached via C=O, and AA¹ attached to N]  x HOAc

| No. | AA¹ | AA² | HPLC t_R (min) | MS MW (calc.) free base | [M + H⁺] (found) |
|---|---|---|---|---|---|
| 8 | [Lysine structure with NH₂ and H₂N] | [aminoisobutyric acid structure] | 3.28 | 328.41 | 329 |
| 9 | [Lysine structure with NH₂ and H₂N] | [tert-leucine structure] | 3.59 | 356.47 | 357 |

TABLE 2-continued

| No. | AA¹ | AA² | HPLC $t_R$ (min) | MW (calc.) free base | MS [M + H⁺] (found) |
|---|---|---|---|---|---|
| 10 | Lys | Aib-NH₂ | 3.28 | 327.43 | 328 |
| 11 | Orn | Aib-OH | 3.39 | 314.39 | 315 |
| 12 | Nle | Aib-OH | 3.90 | 313.40 | 314 |
| 13 | Phe | Aib-OH | 3.98 | 347.42 | 348 |
| 14 | N-Me-Phe | Aib-OH | 3.33 | 361.44 | 362 |
| 15 | D-Phe | Aib-OH | 3.56 | 347.42 | 348 |

TABLE 2-continued

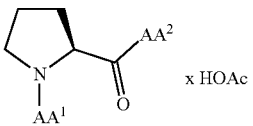

x HOAc

| No. | AA¹ | AA² | HPLC $t_R$ (min) | MW (calc.) free base | MS [M + H⁺] (found) |
|---|---|---|---|---|---|
| 16 | 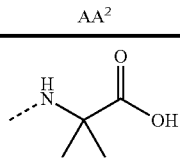 | | 3.23 | 341.45 | 342 |
| 17 | 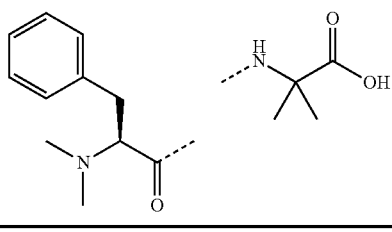 | | 3.30 | 375.47 | 376 |

Biological Assays

A. Cytokine Secretion on Protein Level and Gene Expression

Primary T-cells were isolated from peripheral blood from healthy volunteers and from secondary lymphatic organs from naïve C57BL/6 mice, respectively. The cells were stimulated with phorbol-12-myristate-13-acetate (PMA)/Ionomycin and interferon-gamma (IFN-γ), respectively, for 48 h to activate the cells. The activated cells release pro-inflammatory cytokines. In parallel a human (HaCaT) keratinocyte cell line was activated with PMA/Ionomycin and IFN-γ, respectively, too. It is known that treatment with PMA/Ionomycin and IFN-γ, respectively, resulted in an increased release of pro-inflammatory cytokines IL-1, IL-2, IL-6, IL-17, IFN-γ or TNF-α. At the same time release of anti-inflammatory IL-10 was inhibited. Two days after addition of PMA/Ionomycin and IFN-γ, respectively, the induction of IL-1 secretion was determined in the supernatant for proving that the cells are activated. Following this the cells were treated with different doses ($10^{-7}$ M, $10^{-9}$ M and $10^{-11}$ M) of the tripeptides, PBS (negative control) and alpha-melanocyte-stimulating hormone (α-MSH), K(D)PT, mycophenolate mofetil (MMF) and dexamethasone, respectively, as positive controls. The anti-inflammatory properties of the tripeptides were determined 48 h and 72 h following stimulation. A 13-plex-system based FACS analysis was used for showing the reduced secretion of pro-inflammatory cytokines in the supernatant. Data for IL-1, IL-2, IL-6, IL-12p70 IL-17, IFN-γ and TNF-α are considered to be most relevant. Thus, analysis of the anti-inflammatory properties of the tripeptides is preferably based on the results obtained for these analytes. Moreover, these results were verified by preparation of mRNA and subsequent RT-qPCR analysis. Using this method the gene expression of pro-inflammatory markers like IL-6, IL-17, IFN-γ and TNF-α was determined.

In a first experiment it was shown that especially Examples 3, 8 and 9 are characterized by showing stronger anti-inflammatory effects compared to the positive control K(D)PT. They were able to reduce the secretion of pro-inflammatory cytokines in activated primary murine and human T-cells as well as in human keratinocytes more efficiently. All tripeptides mentioned above inhibited the secretion of at least three of the analyzed pro-inflammatory cytokines (IL-1, IL-2, IL-6, IL-17, IFN-γ or TNF-α) to a larger extend than the positive control K(D)PT. In addition an induction of the secretion of anti-inflammatory cytokine IL-10 was observed in keratinocytes (Tables 3-5). Treatment with Examples 1 and 2 resulted in a decreased secretion of pro-inflammatory cytokines in keratinocytes.

Results obtained by determining the cytokine data from the supernatants were confirmed on gene expression level for Examples 3, 8 and 9. RT-qPCR experiments revealed immunomodulatory activities of Examples 3 and 8 comparable to K(D)PT which served as positive control. mRNA expression of IL-6, IL-17, IFN-γ and TNF-α was reduced in human and murine T cells following stimulation with the compounds. Moreover, treatment with Examples 3, 8 and 9 was associated with a reduction of the gene expression of pro-inflammatory cytokines in HaCaT keratinocytes (FIGS. 1-3).

In a second experiment it was show that Example 12 was able to reduce the expression of pro-inflammatory cytokines in all three cellular models. The activity was comparable with the one of K(D)PT. Treatment with Examples 6 and 13 resulted in a decreased expression of pro-inflammatory cytokines in human T cells and keratinocytes. For Examples 5 and 7 immunomodulatory effects were seen in human and murine T cells (Tables 6-8).

Expression of genes coding for pro-inflammatory markers like IL-6, IL-17, IFN-γ and TNF-α was determined as described above. It was shown that stimulation with Example 13 resulted in a reduced expression of pro-inflammatory markers in all stimulated cells (FIGS. 4-6).

In a third experiment murine and human T cells and HaCaT cells were stimulated with PMA/Ionomycin and treated with Examples 14, 15, 16 and 17 at $10^{-7}$ M, $10^{-9}$ M and $10^{-11}$ M. Cytokine concentrations (IFN-γ, IL-17 and IL-10 for T cells and IFN-γ for HaCat) were assessed in the supernatants using the Luminex technology. Expression of genes coding for Il-1β, IL-6 and TNF-α was determined. Treatment with Examples 14, 15, 16 and 17 resulted in reduced expression of pro-inflammatory cytokines IL-1β, IL-6 and TNF-α on mRNA level in all cell types and at all concentrations tested. Moreover, concentrations of pro-inflammatory cytokines IFN-γ and IL-17 was reduced in the supernatants whereas the concentration of anti-inflammatory cytokine IL-10 was increased. Again, this was observed for all tested concentrations.

The anti-inflammatory and immunomodulatory effects of selected examples of the present invention were compared with common immunosuppressants. Thus, cells activated with PMA/Ionomycin and IFN-γ, respectively, were stimulated with MMF or dexamethasone. Following stimulation the secretion of pro-inflammatory cytokines was analyzed on protein and gene level (Table 9 and FIGS. 4-6). Surprisingly, it was found that Example 13 showed an immunomodulatory activity higher than the one observed for MMF.

For the biological assay two human cell lines of different origin were chosen to allow for translation of the results obtained. A HaCaT cell is a cell type belonging to an immortal human keratinocyte line used in scientific research. Its use in research allows for the characterization of human keratinocyte using a model that is reproducible and representing a human epithelial cell line. In contrast human T-lymphocytes (T-cells) are a type of lymphocyte (itself a type of white blood cell) that play a central role in cell-mediated inflammation/immunity.

TABLE 3

Cytokine expression in primary human T-cells following activation with PMA/Ionomycin and IFN-γ, respectively, and stimulation with Examples 1-3, 8 and 9 (concentration: $10^{-9}$M).

| Substance | IL-13 | IL-1 | IL-22 | IL-2 | IL-5 | IL-9 | IL-6 | IL-10 | IL-12p70 | IFN-γ | TNF-α | IL-4 | IL-17 |
|---|---|---|---|---|---|---|---|---|---|---|---|---|---|
| primary human T-cells stimulated with PBS, cytokine concentration [pg/ml] | | | | | | | | | | | | | |
| PBS | 95.32 | 339.39 | 2219.03 | 643.96 | 45.25 | 138.06 | 137.97 | 102.88 | 192.2 | 918.8 | 233.5 | 156.14 | 269.73 |
| α-MSH | 74.71 | 233.71 | 2258.05 | 166.83 | 26.63 | 93.72 | 103.97 | 154.89 | 100.99 | 584.13 | 127.96 | 158.58 | 123.27 |
| K(D)PT | 80.48 | 268.37 | 0 | 435.34 | 0 | 102.2 | 92.39 | 126.13 | 114.67 | 610.05 | 160.25 | 136.29 | 182.45 |
| Example 1 | 77.6 | 398.01 | 2227.62 | 545.22 | 275.55 | 131.69 | 85.95 | 107.07 | 223.67 | 634.2 | 203.95 | 198.06 | 295.13 |
| Example 2 | 90.3 | 305.62 | 2242.06 | 985.16 | 310.87 | 116.55 | 84.38 | 253.29 | 226.23 | 0 | 211.85 | 151.33 | 238.4 |
| Example 8 | 67.68 | 253.83 | 2211.56 | 237.8 | 61.66 | 93.72 | 72.63 | 114.3 | 94.18 | 0 | 132.37 | 117.83 | 116.91 |
| Example 9 | 91.02 | 398.01 | 2258.05 | 298.65 | 68.35 | 93.72 | 98.42 | 210.15 | 210.63 | 1111.58 | 258.09 | 151.99 | 253.52 |
| Example 3 | 88.14 | 233.69 | 2185.25 | 317.62 | 42.46 | 111.16 | 61.21 | 47.15 | 103.5 | 450.32 | 190.58 | 161.66 | 153.86 |
| primary human T-cells stimulated with PMA/Ionomycin, cytokine concentration [pg/ml] | | | | | | | | | | | | | |
| PBS | 821.24 | 22302.1 | 23424.4 | 12000 | 376.68 | 148.81 | 1641.55 | 4620.87 | 1717 | 3585.27 | 3600 | 232.58 | 2391.49 |
| α-MSH | 462.62 | 69689.2 | 24400.4 | 12000 | 145.89 | 187.5 | 1542.01 | 4311.06 | 1161.04 | 1049.41 | 3600 | 200.9 | 2836.14 |
| K(D)PT | 944.87 | 69689.2 | 24079 | 12000 | 173.34 | 162.4 | 2058.24 | 4936.79 | 1703.5 | 1854.29 | 3600 | 235.78 | 3116.43 |
| Example 1 | 398.98 | 11244.1 | 24324.9 | 12000 | 204.84 | 159.86 | 1868.8 | 3032.66 | 925.71 | 2516.08 | 3600 | 209.61 | 2443.34 |
| Example 2 | 760.63 | 69689.2 | 24128.2 | 12000 | 325.76 | 142.93 | 1533.99 | 3938.15 | 1413.17 | 2726.77 | 3600 | 239.02 | 3476.92 |
| Example 8 | 475.53 | 69689.2 | 24669.3 | 12000 | 215.28 | 183.92 | 2131.81 | 4027.17 | 867.26 | 1774.79 | 3600 | 204.5 | 2943.03 |
| Example 9 | 827 | 1331.79 | 24198 | 12000 | 114.01 | 157.98 | 1759.4 | 4514.53 | 822.84 | 3589.9 | 3600 | 236.59 | 2531.57 |
| Example 3 | 400.36 | 69689.2 | 24185.6 | 12000 | 234.91 | 166.27 | 1965.67 | 3588.06 | 766.66 | 1182.71 | 3600 | 237.39 | 2796.62 |
| primary human T-cells stimulated with IFN-γ, cytokine concentration [pg/ml] | | | | | | | | | | | | | |
| PBS | 107.38 | 595.78 | 0 | 809.25 | 222.07 | 121.11 | 130.74 | 86.19 | 1973.85 | | 337.28 | 205.22 | 298.66 |
| α-MSH | 59.46 | 229 | 0 | 0 | 145.89 | 90.3 | 70.19 | 109.15 | 727.17 | | 155.15 | 136.29 | 125.8 |
| K(D)PT | 72.09 | 335.73 | 22747.7 | 79.24 | 249.7 | 93.74 | 93.02 | 169.54 | 895.95 | | 178.65 | 184.31 | 204.05 |
| Example 1 | 82.57 | 296.42 | 21389.5 | 515.89 | 112.65 | 111.14 | 131.33 | 164.32 | 945.16 | | 230.57 | 180.24 | 234.65 |
| Example 2 | 97.39 | 314.88 | 21970.6 | 740.3 | 177.72 | 106.37 | 97.68 | 146.79 | 804.93 | | 188.29 | 116.26 | 168.9 |
| Example 8 | 75.98 | 277.33 | 22151.4 | 199.66 | 91.09 | 88.6 | 95.92 | 106.23 | 688.46 | | 171.54 | 117.31 | 118.21 |
| Example 9 | 79.89 | 363.19 | 0 | 164.47 | 52.14 | 97.68 | 90.63 | 154.92 | 704.53 | | 178.78 | 141.97 | 184.81 |
| Example 3 | 75.98 | 191.46 | 0 | 144.56 | 95.22 | 103.58 | 65.54 | 87.89 | 687.61 | | 180.13 | 132.38 | 110.07 |

Assays in which the cytokine concentration in the supernatant was below the limit of detection are marked gray. Gray hatched cells indicated assays in which cytokine quantification is compromised due to the stimulant.

TABLE 4

Cytokine expression in a human keratinocyte cell line (HaCaT) following activation with PMA/Ionomycin and IFN-γ, respectively, and stimulation with Examples 1-3, 8 and 9 (concentration: $10^{-9}$M).

| Substance | IL-13 | IL-1 | IL-22 | IL-2 | IL-5 | IL-9 | IL-6 | IL-10 | IL-12p70 | IFN-γ | TNF-α | IL-4 | IL-17 |
|---|---|---|---|---|---|---|---|---|---|---|---|---|---|
| HaCaT stimulated with PBS, cytokine concentration [pg/ml] | | | | | | | | | | | | | |
| PBS | 91.64 | 381.59 | 12968.62 | 524.07 | 343.72 | 126.98 | 179.5 | 124.72 | 1910.23 | 728.9 | 228.16 | 87.68 | 817.55 |
| α-MSH | 65.47 | 271.66 | 9847.56 | 251.78 | 150.8 | 124.69 | 76.75 | 107.72 | 0 | 365.47 | 97.16 | 56.84 | 544.96 |
| K(D)PT | 60.72 | 228.99 | 10982.2 | 201.9 | 201.01 | 132.74 | 72.95 | 125.52 | 0 | 395.55 | 90.41 | 85.48 | 618.22 |
| Example 1 | 64.17 | 224.9 | 18087.5 | 87.98 | 181.61 | 112.82 | 77.53 | 166.47 | 1881.61 | 373.53 | 87.84 | 85.92 | 562.61 |
| Example 2 | 69.36 | 251.25 | 14446.9 | 177.85 | 189.12 | 139.65 | 75.53 | 151.26 | 1864.02 | 397.45 | 84.84 | 90.8 | 569.9 |
| Example 8 | 75.26 | 227.07 | 17754.7 | 194.17 | 191.65 | 83.09 | 69.88 | 104.27 | 0 | 319.39 | 78.12 | 62.6 | 627.77 |

TABLE 4-continued

Cytokine expression in a human keratinocyte cell line (HaCaT) following activation with PMA/Ionomycin and IFN-γ, respectively, and stimulation with Examples 1-3, 8 and 9 (concentration: $10^{-9}$ M).

| Substance | IL-13 | IL-1 | IL-22 | IL-2 | IL-5 | IL-9 | IL-6 | IL-10 | IL-12p70 | IFN-γ | TNF-α | IL-4 | IL-17 |
|---|---|---|---|---|---|---|---|---|---|---|---|---|---|
| Example 9 | 56.83 | 232.45 | 15532.1 | 188.4 | 132.61 | 121.47 | 81.84 | 17702 | 1914.52 | 330.74 | 91.82 | 82.9 | 605.66 |
| Example 3 | 56.84 | 228.09 | 16936.8 | 163.98 | 154.73 | 130.34 | 85.65 | 46.71 | 1910.22 | 389.43 | 74.7 | 71.68 | 585.63 |
| HaCaT stimulated with PMA/Ionomycin, cytokine concentration [pg/ml] | | | | | | | | | | | | | |
| PBS | 108.92 | 458.36 | 18106.91 | 505.37 | 330.93 | 152.65 | 198.42 | 217.92 | 1879.36 | 1420.36 | 155.44 | 99.96 | 774.54 |
| α-MSH | 55.34 | 143.16 | 9995.76 | 98.72 | 131.91 | 105.55 | 113.54 | 111.19 | 0 | 617.26 | 103.98 | 72.6 | 338.9 |
| K(D)PT | 62.95 | 212.49 | 10698.1 | 179.25 | 157.36 | 147.79 | 130.87 | 84.32 | 0 | 736.13 | 116.88 | 70.92 | 487.56 |
| Example 1 | 49.03 | 118.79 | 8956.12 | 108.97 | 141.02 | 108.97 | 108.97 | 48.13 | 0 | 531 | 77.12 | 78.12 | 449.68 |
| Example 2 | 69.36 | 204.23 | 14806.4 | 130.08 | 129.65 | 104.14 | 129.99 | 97.55 | 0 | 704.33 | 62.15 | 58.48 | 369.01 |
| Example 8 | 53.79 | 190.71 | 12874.7 | 49.76 | 157.68 | 124.07 | 120.62 | 42.93 | 0 | 642.47 | 67.78 | 76.85 | 457.23 |
| Example 9 | 65.15 | 208.59 | 17795 | 113.83 | 162.04 | 129.3 | 131.98 | 153.24 | 0 | 738.89 | 89.8 | 57.66 | 446.55 |
| Example 3 | 61.45 | 197.77 | 17177.7 | 150.8 | 144.76 | 128.88 | 187.91 | 0 | 720.85 | 88.62 | 60.13 | 397.57 | |
| HaCaT stimulated with IFN-γ, cytokine concentration [pg/ml] | | | | | | | | | | | | | |
| PBS | 87.68 | 392.3 | 18326.9 | 301.9 | 252.26 | 102.27 | 1030.02 | 57.84 | 1987.25 | | 215.66 | 103.92 | 899.01 |
| α-MSH | 55.34 | 238.96 | 0 | 119.87 | 184.1 | 83.5 | 750.84 | 82.71 | 0 | | 67.75 | 70.08 | 598.13 |
| K(D)PT | 59.62 | 257.77 | 0 | 129.65 | 166.92 | 83.09 | 728.31 | 73.19 | 0 | | 100.07 | 84.61 | 664.43 |
| Example 1 | 57.99 | 251.36 | 18014.5 | 95.81 | 156.74 | 96.1 | 704.01 | 107.72 | 1872.11 | | 101.29 | 88.93 | 612.41 |
| Example 2 | 61.18 | 265.46 | 0 | 96.34 | 109.73 | 104.08 | 641.89 | 129.2 | 1904.09 | | 79.97 | 71.76 | 629.16 |
| Example 8 | 51.17 | 245.46 | 17253.8 | 111.78 | 159.55 | 98.35 | 633.6 | 102.56 | 1789.21 | | 92.08 | 84.09 | 592.65 |
| Example 9 | 54.12 | 245.47 | 18682.2 | 108.74 | 121.18 | 108.39 | 630.85 | 156.25 | 1806.39 | | 86.98 | 79.04 | 661.44 |
| Example 3 | 58.79 | 239.94 | 19411 | 130.32 | 111.33 | 98.44 | 606.47 | 107.71 | 1843.69 | | 100.94 | 80.39 | 642.41 |

Assays in which the cytokine concentration in the supernatant was below the limit of detection are marked gray. Gray hatched cells indicated assays in which cytokine quantification is compromised due to the stimulant. Values for IL-22 and IL-12p70 were excluded from the final assessment of anti-inflammatory activity.

TABLE 5

Cytokine expression in primary murine T-cells following activation with PMA/Ionomycin and IFN-γ, respectively, and stimulation with Examples 1-3, 8 and 9 (concentration: $10^{-9}$ M).

| Substance | IL-13 | IL-1 | IL-22 | IL-2 | IL-5 | IL-21 | IL-6 | IL-10 | IL-27 | IFN-γ | TNF-α | IL-4 | IL-17 |
|---|---|---|---|---|---|---|---|---|---|---|---|---|---|
| primary murine T-cells stimulated with PBS, cytokine concentration [pg/ml] | | | | | | | | | | | | | |
| PBS | 0 | 0 | 0 | 115.05 | 0 | 0 | 33.87 | 19.11 | 127.16 | 0 | 0 | 0 | 29.47 |
| α-MSH | 0 | 0 | 0 | 0 | 0 | 0 | 16.44 | 55.47 | 0 | 0 | 0 | 0 | 0 |
| K(D)PT | 0 | 0 | 0 | 0 | 0 | 0 | 27.81 | 64.53 | 25.93 | 0 | 0 | 0 | 16.26 |
| Example 1 | 0 | 53.09 | 0 | 0 | 0 | 0 | 0 | 110.76 | 379.78 | 0 | 0 | 0 | 0 |
| Example 2 | 0 | 36.6 | 0 | 138.15 | 45.71 | 0 | 0 | 0 | 0 | 2375.02 | 0 | 0 | 0 |
| Example 8 | 0 | 0 | 0 | 0 | 0 | 0 | 14.65 | 68.32 | 881.79 | 0 | 0 | 0 | 0 |
| Example 9 | 0 | 0 | 0 | 0 | 10.13 | 0 | 14.65 | 0 | 727.44 | 0 | 0 | 0 | 0 |
| Example 3 | 0 | 14.89 | 0 | 0 | 0 | 0 | 0 | 40.84 | 268.47 | 0 | 0 | 0 | 0 |
| primary murine T-cells stimulated with PMA/Ionomycin, cytokine concentration [pg/ml] | | | | | | | | | | | | | |

| Substance | IL-13 | IL-1 | IL-22 | IL-2* | IL-5 | IL-21 | IL-6 | IL-10 | IL-27 | IFN-γ* | TNF-α | IL-4 | IL-17 |
|---|---|---|---|---|---|---|---|---|---|---|---|---|---|
| PBS | 4162.87 | 70.12 | 630.86 | 3133.92 | 370.79 | 0 | 273.3 | 189.43 | 280.91 | 4397.44 | 520.47 | 71.79 | 596.87 |
| α-MSH | 3966.69 | 28.92 | 356.41 | 849.44 | 262.76 | 0 | 114.47 | 276.06 | 0 | 0 | 535.51 | 0 | 311.07 |
| K(D)PT | 4314.15 | 30.27 | 333.4 | 1288.92 | 280.87 | 0 | 140.97 | 188.56 | 99.7 | 712.81 | 515.54 | 71.79 | 423.67 |
| Example 1 | 3898.42 | 60.61 | 526.42 | 1354.76 | 292.17 | 0 | 239.47 | 145.26 | 426.79 | 0 | 535.51 | 0 | 459.99 |
| Example 2 | 4703.82 | 0 | 670.15 | 744.58 | 350.49 | 0 | 338.28 | 155.42 | 778.4 | 0 | 628.15 | 129.47 | 649.14 |
| Example 8 | 5324.44 | 0 | 550.32 | 1576.19 | 225.53 | 0 | 283.79 | 230.31 | 226.79 | 0 | 598.72 | 86 | 511.02 |
| Example 9 | 6704.42 | 0 | 571.55 | 1958.61 | 281.76 | 0 | 276.29 | 332.03 | 368.78 | 4197.73 | 590.89 | 120.33 | 547.87 |
| Example 3 | 6629.52 | 49.31 | 554.05 | 3973.68 | 377 | 0 | 218.74 | 270.65 | 0 | 4716.4 | 544.83 | 82.28 | 535.72 |
| primary murine T-cells stimulated with IFN-γ, cytokine concentration [pg/ml] | | | | | | | | | | | | | |

| | IL-13 | IL-1 | IL-22 | IL-2 | IL-5 | IL-21 | IL-6 | IL-10 | IL-27 | IFN-γ | TNF-α | IL-4 | IL-17 |
|---|---|---|---|---|---|---|---|---|---|---|---|---|---|
| PBS | 0 | 62.92 | 0 | 0 | 86.8 | 0 | 0 | 0 | 504.57 | | 10.29 | 0 | 0 |
| α-MSH | 0 | 14.89 | 0 | 0 | 0 | 0 | 0 | 0 | 0 | | 0 | 0 | 0 |
| K(D)PT | 0 | 26.6 | 0 | 0 | 0 | 0 | 0 | 0 | 209.12 | | 0 | 0 | 0 |
| Example 1 | 0 | 0 | 0 | 0 | 0 | 0 | 6.51 | 0 | 179.72 | | 0 | 0 | 10.81 |
| Example 2 | 0 | 22.78 | 8.52 | 0 | 72.11 | 0 | 23.14 | 72.95 | 1234.48 | | 0 | 0 | 0 |
| Example 8 | 84.63 | 47.84 | 0 | 0 | 72.14 | 0 | 29.32 | 59.11 | 404.38 | | 0 | 0 | 0 |

TABLE 5-continued

Cytokine expression in primary murine T-cells following activation with PMA/Ionomycin and IFN-γ, respectively, and stimulation with Examples 1-3, 8 and 9 (concentration: $10^{-9}$M).

| Example 9 | 0 | 73.28 | 0 | 0 | 0 | 0 | 16.44 | 0 | 99.7 | | 0 | 0 |
| Example 3 | 0 | 0 | 0 | 0 | 0 | 0 | 0 | 68.31 | 555.75 | 0 | 0 | 0 |

Assays in which the cytokine concentration in the supernatant was below the limit of detection are marked gray. Gray hatched cells indicated assays in which cytokine quantification is compromised due to the stimulant.
*Values for IL-2 and IFN-γ were above 20,000 pg/ml in the supernatants following activation with PMA/Ionomycin. Thus, a 1:10 dilution of the supernatants was prepared for these assays.

TABLE 6

Cytokine expression in primary human T-cells following activation with PMA/Ionomycin and IFN-γ, respectively, and stimulation with Examples 4-7 and 10-13 (concentration: $10^{-9}$M).

| Substance | IL-12p70 | INF-α | IL-17 | IL-2 | IL-10 | IL-9 | IL-22 | IL-6 | IL-13 | IL-4 | IL-5 | IL-1 | TNF-α |
|---|---|---|---|---|---|---|---|---|---|---|---|---|---|
| primary human T-cells stimulated with PBS, cytokine concentration [pg/ml] | | | | | | | | | | | | | |
| PBS | 0 | 558.41 | 268.55 | 302.37 | 123.94 | 95.58 | 0 | 198.34 | 285.36 | 186.54 | 164.77 | 433.48 | 113.92 |
| α-MSH | 0 | 0 | 139.74 | 139.68 | 164.01 | 34.99 | 0 | 117.88 | 185.71 | 72.42 | 14.37 | 0 | 59.06 |
| K(D)PT | 0 | 0 | 127.21 | 0 | 159.09 | 0 | 0 | 109.89 | 172.66 | 0 | 0 | 147.97 | 65.47 |
| Example 10 | 0 | 0 | 0 | 0 | 48.86 | 23.18 | 0 | 216.7 | 0 | 0 | 0 | 0 | 21.65 |
| Example 11 | 0 | 505.68 | 0 | 0 | 0 | 10.84 | 0 | 172.14 | 187.86 | 121.69 | 0 | 0 | 52.55 |
| Example 12 | 0 | 0 | 104.68 | 0 | 189.65 | 0 | 0 | 91.86 | 0 | 0 | 0 | 0 | 41.38 |
| Example 13 | 0 | 0 | 65.17 | 115.73 | 147.54 | 10.84 | 0 | 113.86 | 0 | 73.19 | 0 | 0 | 50.36 |
| Example 4 | 0 | 0 | 0 | 0 | 0 | 3.71 | 0 | 226.2 | 0 | 60.49 | 0 | 122.89 | 0 |
| Example 5 | 0 | 0 | 0 | 0 | 119.04 | 6.74 | 0 | 94.11 | 35.75 | 0 | 0 | 0 | 0 |
| Example 6 | 0 | 0 | 113.52 | 114.93 | 92.62 | 8.15 | 0 | 105.53 | 0 | o | 12.74 | 107.12 | 28.11 |
| Example 7 | 0 | 69.17 | 95.69 | 126.59 | 121.25 | 13.42 | 0 | 122.64 | 0 | 0 | 8.58 | 154.31 | 51.46 |
| primary human T-cells stimulated with PMA/Ionomycin, cytokine concentration [pg/ml] | | | | | | | | | | | | | |
| PBS | 0 | 20668.73 | 3370.25 | 10549.5 | 802.68 | 767.48 | 0 | 2981.92 | 1864.96 | 112.94 | 506.89 | 985.31 | 8233.81 |
| α-MSH | 0 | 10814.35 | 1660.92 | 2307.5 | 977.83 | 264.59 | 0 | 1241.17 | 1065.69 | 70.32 | 278.92 | 530.55 | 3346.46 |
| K(D)PT | 0 | 12070.42 | 1808.01 | 3486.84 | 877.54 | 332.07 | 0 | 1535.49 | 1158.74 | 41.83 | 379.39 | 594.38 | 3998.01 |
| Example 10 | 0 | 11538.53 | 2234.39 | 5107.74 | 729.43 | 461.98 | 0 | 1255.58 | 1183.46 | 179.62 | 416.25 | 878.53 | 4132.03 |
| Example 11 | 0 | 9554.27 | 3306.09 | 3920.52 | 563.89 | 380.3 | 0 | 1474.06 | 1258.74 | 112.94 | 525.15 | 677.32 | 2209.22 |
| Example 12 | 0 | 9454.26 | 1355.07 | 2751.28 | 992.02 | 286.89 | 0 | 1046.79 | 1026.08 | 73.38 | 328.24 | 548.85 | 2985.72 |
| Example 13 | 0 | 7456.27 | 1069.51 | 2092.22 | 872.88 | 248.66 | 0 | 1185.87 | 1081.09 | 0 | 354.06 | 558.46 | 2706.11 |
| Example 4 | 0 | 5384.11 | 1356.78 | 1227.93 | 417.95 | 239.43 | 0 | 1280 | 1081.09 | 239.37 | 473.23 | 689.99 | 4112.99 |
| Example 5 | 0 | 8770.62 | 1164.75 | 4369.09 | 789.38 | 193.58 | 0 | 1051.51 | 912.49 | 92.43 | 392.66 | 748 | 2187.46 |
| Example 6 | 0 | 7597.87 | 1388.88 | 2005.81 | 999.32 | 238.28 | 0 | 1194.58 | 1050.19 | 87.24 | 312.5 | 533.57 | 2638.52 |
| Example 7 | 0 | 6989.26 | 2611.96 | 1650.58 | 842.93 | 263.36 | 0 | 1100.07 | 991.61 | 72.07 | 357.88 | 508.96 | 2062.57 |
| primary human T-cells stimulated with IFN-γ, cytokine concentration [pg/ml] | | | | | | | | | | | | | |
| PBS | 0 | 120.31 | 178.78 | 0 | 15.92 | 0 | 104.38 | 187.86 | 134.71 | 117.9 | 79.74 | 73.01 | |
| α-MSH | 0 | 0 | 0 | 43.9 | 5.27 | 0 | 64.54 | 0 | 60.49 | 0 | 0 | 18.85 | |
| K(D)PT | 0 | 0 | 0 | 33.21 | 9.51 | 0 | 58.47 | 0 | 0 | 0 | 0 | 0 | |
| Example 10 | 0 | 250.1 | 231.83 | 0 | 0 | 0 | 105.21 | 162.81 | 160.97 | 0 | 139.49 | 0 | |
| Example 11 | 0 | 0 | 212.98 | 50.11 | 8.15 | 0 | 108.08 | 180.41 | 0 | 83.3 | 0 | 52.55 | |
| Example 12 | 0 | 0 | 0 | 84.25 | 7.67 | 0 | 60.44 | 0 | 0 | 0 | 44.77 | 41.38 | |
| Example 13 | 0 | 81.59 | 187.16 | 0 | 0 | 0 | 60.51 | 0 | 0 | 0 | 15.32 | 162.75 | |
| Example 4 | 0 | 162.73 | 326.11 | 75.72 | 10.84 | 0 | 180.43 | 212.64 | 176.6 | 27.34 | 366.09 | 103.24 | |
| Example 5 | 0 | 26.44 | 0 | 61 | 5.56 | 0 | 42.52 | 29.25 | 78.18 | 0 | 0 | 12.52 | |
| Example 6 | 0 | 36.76 | 0 | 51.86 | 0 | 0 | 45.83 | 46.95 | 76.04 | 0 | 0 | 17.44 | |
| Example 7 | 0 | 0 | 0 | 69.21 | 0 | 0 | 56.38 | 59.7 | 83.34 | 0 | 0 | 0 | |

Assays in which the cytokine concentration in the supernatant was below the limit of detection are marked gray. Gray hatched cells indicated assays in which cytokine quantification is compromised due to the stimulant.

TABLE 7

Cytokine expression in a human keratinocyte cell line (HaCaT) following activation with PMA/Ionomycin and IFN-γ, respectively, and stimulation with Examples 4-7 and 10-13 (concentration: $10^{-9}$M).

| Substance | IL-12p70 | IFN-γ | IL-17 | IL-2 | IL-10 | IL-9 | IL-22 | IL-6 | IL-13 | IL-4 | IL-5 | IL-1 | TNF-α |
|---|---|---|---|---|---|---|---|---|---|---|---|---|---|
| HaCaT stimulated with PBS, cytokine concentration [pg/ml] | | | | | | | | | | | | | |
| PBS | 0 | 391.65 | 45.41 | 233.68 | 32.84 | 18.84 | 0 | 182.52 | 1910.23 | 229.6 | 51.29 | 195.08 | 38.87 |
| α-MSH | 0 | 0 | 0 | 0 | 39.54 | 9.51 | 0 | 15.22 | 0 | 118.52 | 0 | 0 | 0 |
| K(D)PT | 0 | 99.65 | 0 | 0 | 31.43 | 5.27 | 0 | 78.34 | 0 | 144.86 | 0 | 65.11 | 9.34 |
| Example 10 | 0 | 469.17 | 230.84 | 0 | 0 | 5.28 | 0 | 125.38 | 1864.02 | 218.04 | 0 | 170.16 | 0 |
| Example 11 | 0 | 0 | 0 | 0 | 43.56 | 1.97 | 0 | 42.94 | 0 | 99.64 | 0 | 0 | 0 |

TABLE 7-continued

Cytokine expression in a human keratinocyte cell line (HaCaT) following activation with PMA/Ionomycin and IFN-γ, respectively, and stimulation with Examples 4-7 and 10-13 (concentration: $10^{-9}$M).

| Substance | IL-12p70 | IFN-γ | IL-17 | IL-2 | IL-10 | IL-9 | IL-22 | IL-6 | IL-13 | IL-4 | IL-5 | IL-1 | TNF-α |
|---|---|---|---|---|---|---|---|---|---|---|---|---|---|
| Example 12 | 0 | 0 | 0 | 0 | 69.45 | 4.96 | 0 | 56.87 | 193.75 | 0 | 0 | 0 | 5.55 |
| Example 13 | 0 | 0 | 0 | 14.24 | 74.67 | 0 | 0 | 74.11 | 1948.04 | 132.37 | 0 | 17.16 | 6.94 |
| Example 4 | 0 | 0 | 12.85 | 18.85 | 61.87 | 2.87 | 0 | 80.55 | 123.68 | 109.04 | 0 | 0 | 0 |
| Example 5 | 0 | 18.83 | 149.51 | 89.86 | 28.51 | 0 | 218.63 | 0 | 152.8 | 133.49 | 0 | 0 | 0 |
| Example 6 | 0 | 0 | 26.72 | 0 | 57.95 | 0 | 0 | 52.48 | 0 | 91.99 | 0 | 25.45 | 8.21 |
| Example 7 | 0 | 0 | 0 | 180.91 | 0 | 0 | 0 | 119.59 | 1910.22 | 0 | 113.28 | 181.03 | 21.66 |
| HaCaT stimulated with PMA/Ionomycin, cytokine concentration [pg/ml] | | | | | | | | | | | | | |
| PBS | 0 | 109.28 | 101.48 | 172.29 | 78.59 | 14.7 | 0 | 422.8 | 1879.36 | 235.96 | 71.04 | 162.79 | 83.03 |
| α-MSH | 0 | 0 | 0 | 0 | 93.2 | 0 | 0 | 179.03 | 0 | 113.12 | 0 | 0 | 0 |
| K(D)PT | 0 | 0 | 0 | 0 | 118.77 | 0 | 0 | 282.85 | 0 | 129.6 | 0 | 0 | 0 |
| Example 10 | 0 | 327.78 | 45.41 | 189.17 | 34.84 | 14.67 | 0 | 315.82 | 0 | 0 | 0 | 251.13 | 53.51 |
| Example 11 | 0 | 57.58 | 0 | 19.32 | 87.41 | 0 | 0 | 207.76 | 0 | 0 | 0 | 0 | 0 |
| Example 12 | 0 | 22.77 | 25.98 | 0 | 86.04 | 0 | 0 | 158.4 | 0 | 0 | 0 | 0 | 0 |
| Example 13 | 0 | 0 | 21.33 | 0 | 41.86 | 0 | 0 | 216.69 | 0 | 91.99 | 0 | 0 | 0 |
| Example 4 | 0 | 39.23 | 28.83 | 0 | 97.56 | 0 | 0 | 225.53 | 0 | 0 | 16.77 | 0 | 3.93 |
| Example 5 | 0 | 199.65 | 95.44 | 145.65 | 59.49 | 0 | 0 | 379.04 | 0 | 168.7 | 1.93 | 104.98 | 27.45 |
| Example 6 | 0 | 0 | 21.52 | 16.53 | 64.03 | 3.71 | 0 | 248.33 | 0 | 0 | 0 | 62.07 | 5.37 |
| Example 7 | 0 | 450.42 | 209.12 | 218.82 | 64.01 | 14.57 | 0 | 359.17 | 1877.03 | 112.94 | 88.67 | 0 | 0 |
| HaCaT stimulated with IFN-γ, cytokine concentration [pg/ml] | | | | | | | | | | | | | |
| PBS | 0 | 196.73 | 263.44 | 43.65 | 18.37 | 0 | 386.69 | 1987.25 | 176.06 | 115.61 | 177.43 | 148.14 | |
| α-MSH | 0 | 95.44 | 0 | 0 | 0 | 0 | 202.37 | 0 | 0 | 0 | 0 | 45.91 | |
| K(D)PT | 0 | 112.82 | 131.59 | 0 | 0 | 0 | 238.12 | 0 | 52.4 | 0 | 0 | 50.44 | |
| Example 10 | 0 | 189.1 | 0 | 0 | 0 | 0 | 346.73 | 1904.09 | 183.12 | 88.64 | 0 | 0 | |
| Example 11 | 0 | 0 | 0 | 0 | 0 | 0 | 265.29 | 989.21 | 0 | 0 | 31.54 | 0 | |
| Example 12 | 0 | 56.13 | 0 | 0 | 0 | 0 | 297.09 | 195.68 | 69.91 | 0 | 9.31 | 0 | |
| Example 13 | 0 | 34.2 | 0 | 7.59 | 0 | 0 | 255.5 | 0 | 76.13 | 0 | 0 | 0 | |
| Example 4 | 0 | 13.16 | 0 | 0 | 0 | 0 | 224.07 | 0 | 0 | 0 | 0 | 0 | |
| Example 5 | 0 | 0 | 0 | 41.86 | 0 | 0 | 415.82 | 1974.31 | 0 | 0 | 0 | 0 | |
| Example 6 | 0 | 0 | 17.47 | 0 | 0 | 0 | 202.37 | 1872.11 | 0 | 0 | 0 | 0 | |
| Example 7 | 0 | 202.45 | 267.78 | 0 | 14.88 | 0 | 470.44 | 1843.69 | 0 | 0 | 109.65 | 0 | |

Assays in which the cytokine concentration in the supernatant was below the limit of detection are marked gray. Gray hatched cells indicated assays in which cytokine quantification is compromised due to the stimulant.

TABLE 8

Cytokine expression in primary murine T-cells following activation with PMA/Ionomycin and IFN-γ, respectively, and stimulation with Examples 4-7 and 10-13 (concentration: $10^{-9}$M).

| Substance | IL-13 | IL-1 | IL-22 | IL-2 | IL-5 | IL-21 | IL-6 | IL-10 | IL-27 | IFN-γ | TNF-α | IL-4 | IL-17 |
|---|---|---|---|---|---|---|---|---|---|---|---|---|---|
| primary murine T-cells stimulated with PBS, cytokine concentration [pg/ml] | | | | | | | | | | | | | |
| PBS | 0 | 97.92 | 91.09 | 248.08 | 440.16 | 275.49 | 214.22 | 843.73 | 117.28 | 4267.72 | 185.09 | 174.31 | 65.48 |
| α-MSH | 0 | 58.5 | 72.14 | 105.75 | 281.14 | 0 | 96.88 | 1157.87 | 77.41 | 0 | 106.1 | 62.93 | 0 |
| K(D)PT | 0 | 60.41 | 78.32 | 124.13 | 373.93 | 0 | 124 | 1039.39 | 87.48 | 0 | 77.74 | 71.69 | 0 |
| Example 10 | 0 | 66.84 | 71.47 | 132.67 | 229.8 | 0 | 177.95 | 923.65 | 0 | 0 | 77.08 | 65.63 | 0 |
| Example 11 | 0 | 75.71 | 66.43 | 204.62 | 459.03 | 0 | 172.33 | 905.76 | 141.82 | 8321.6 | 0 | 0 | 0 |
| Example 12 | 0 | 61.52 | 76.71 | 189.72 | 331.87 | 69.64 | 223.98 | 872.36 | 71.85 | 0 | 74.9 | 32.24 | 0 |
| Example 13 | 0 | 64.4 | 0 | 173.84 | 401.21 | 0 | 168.6 | 829.52 | 302.6 | 5058.59 | 62.22 | 25.55 | 0 |
| Example 4 | 0 | 78.5 | 84.16 | 147.3 | 377.16 | 330.42 | 189.26 | 1006.65 | 329.85 | 2456.98 | 18.91 | 119.19 | 0 |
| Example 5 | 0 | 56.42 | 27.66 | 151.25 | 209.32 | 13.71 | 117.95 | 1311.94 | 81.64 | 232.8 | 32.89 | 53.6 | 0 |
| Example 6 | 0 | 106.27 | 16.55 | 204.71 | 407.29 | 0 | 170.46 | 1391.3 | 108.06 | 546.71 | 0 | 39.23 | 0 |
| Example 7 | 0 | 62.38 | 15.86 | 137.05 | 317.47 | 0 | 129.26 | 1283.71 | 61.43 | 0 | 53.67 | 60.56 | 0 |
| primary murine T-cells stimulated with PMA/Ionomycin, cytokine concentration [pg/ml] | | | | | | | | | | | | | |
| PBS | 28.32 | 394.58 | 637.02 | 478.56 | 473.93 | 112.39 | 310.34 | 920.36 | 276.49 | 10860.7 | 162.21 | 142.94 | 307.43 |
| α-MSH | 0 | 217.32 | 143.37 | 163.19 | 215.44 | 0 | 174.22 | 1250.21 | 104.52 | 1458.12 | 77.76 | 91.65 | 29.47 |
| K(D)PT | 0 | 175.59 | 90.3 | 152.69 | 238.08 | 0 | 201.87 | 1133.29 | 126.71 | 2117.29 | 49.63 | 72.07 | 70.93 |
| Example 10 | 0 | 173.61 | 44.47 | 179.75 | 267.52 | 0 | 164.16 | 1182.68 | 8.48 | 2377.98 | 33.37 | 56.84 | 86.12 |
| Example 11 | 0 | 178.78 | 94.31 | 261.53 | 513.39 | 0 | 333.86 | 1302.16 | 99.05 | 2756.75 | 86.61 | 117.11 | 244.88 |
| Example 12 | 0 | 167.79 | 57.07 | 98.57 | 242.24 | 0 | 116.16 | 1255.25 | 80.09 | 1298.02 | 50.73 | 90.14 | 79.1 |
| Example 13 | 0 | 329.99 | 111.64 | 260.49 | 452.71 | 432.64 | 404.54 | 1267.4 | 387.94 | 8109.91 | 69.4 | 135.41 | 0 |
| Example 4 | 0 | 196.76 | 48.93 | 292.52 | 465.44 | 987.02 | 245.96 | 1383.24 | 80.01 | 3234.33 | 62.85 | 123.15 | 391.98 |
| Example 5 | 0 | 178.79 | 29.38 | 112.62 | 246.42 | 67.28 | 189.2 | 1233.45 | 51.58 | 2075.42 | 29.15 | 81.4 | 0 |
| Example 6 | 0 | 486.85 | 85.67 | 218.69 | 380.37 | 470.65 | 237.95 | 988.64 | 95.51 | 8164.35 | 72.81 | 164.69 | 200.32 |
| Example 7 | 0 | 154.26 | 71.09 | 99.71 | 246.42 | 0 | 184.98 | 1233.22 | 90.15 | 1916.21 | 40.87 | 99.12 | 67.92 |

TABLE 8-continued

Cytokine expression in primary murine T-cells following activation with PMA/Ionomycin and IFN-γ, respectively, and stimulation with Examples 4-7 and 10-13 (concentration: $10^{-9}$M).

primary murine T-cells stimulated with IFN-γ, cytokine concentration [pg/ml]

| Substance | IL-13 | IL-1 | IL-22 | IL-2 | IL-5 | IL-21 | IL-6 | IL-10 | IL-27 | IFN-γ | TNF-α | IL-4 | IL-17 |
|---|---|---|---|---|---|---|---|---|---|---|---|---|---|
| PBS | 0 | 159.07 | 75.55 | 163.26 | 452.71 | 41.32 | 266.16 | 867.48 | 282.91 | | 75.69 | 195.06 | 154.59 |
| α-MSH | 0 | 88.22 | 50.6 | 96.1 | 220.39 | 0 | 133.9 | 1117.07 | 104.04 | | 36.8 | 20.56 | 55.11 |
| K(D)PT | 0 | 93.77 | 48.13 | 98.22 | 271.81 | 0 | 144.97 | 1061 | 0 | | 34.84 | 85.32 | 88.84 |
| Example 10 | 0 | 77.81 | 57.35 | 93.19 | 238.38 | 0 | 139.83 | 2024.06 | 1.29 | | 32.42 | 81.11 | 0 |
| Example 11 | 0 | 100.08 | 31.59 | 208.9 | 531.87 | 263.02 | 193.06 | 1383.43 | 42.99 | | 19.71 | 53.65 | 39.84 |
| Example 12 | 0 | 86.08 | 42.98 | 88.9 | 221.57 | 40.2 | 110.7 | 1130.01 | 12.5 | | 31.88 | 34.22 | 72.21 |
| Example 13 | 0 | 82.68 | 334.1 | 237.05 | 342.32 | 0 | 220.06 | 968.94 | 151.6 | | 52.48 | 0 | 26.88 |
| Example 4 | 0 | 100.01 | 114.68 | 206.76 | 486.86 | 814.33 | 235.86 | 1250.21 | 138.81 | | 47.36 | 0 | 92.71 |
| Example 5 | 0 | 49.65 | 32.03 | 89.76 | 263.27 | 0 | 127.92 | 1359.92 | 20.07 | | 24.23 | 47.55 | 97.22 |
| Example 6 | 0 | 95.15 | 73.27 | 181.25 | 517.47 | 251.06 | 223.98 | 1782.7 | 0 | | 40.87 | 156.84 | 189.88 |
| Example 7 | 0 | 88.23 | 50.37 | 98.22 | 265.4 | 0 | 123.98 | 1199.53 | 0 | | 25.58 | 40.87 | 84.26 |

Assays in which the cytokine concentration in the supernatant was below the limit of detection are marked gray. Gray hatched cells indicated assays in which cytokine quantification is compromised due to the stimulant.

TABLE 9

Cytokine expression in murine and human cells following activation with PMA/Ionomycin and IFN-γ, respectively, and stimulation with the negative control (PBS) and α-MSH, K(D)PT, MMF and dexamethasone (concentration: $10^{-9}$M).

primary murine T-cells stimulated with PBS, cytokine concentration [pg/ml]

| Substance | IL-13 | IL-1 | IL-22 | IL-2 | IL-5 | IL-21 | IL-6 | IL-10 | IL-27 | IFN-γ | TNF-α | IL-4 | IL-17 |
|---|---|---|---|---|---|---|---|---|---|---|---|---|---|
| PBS | 0 | 97.92 | 91.09 | 248.08 | 440.16 | 275.49 | 214.22 | 843.73 | 117.28 | 4267.72 | 185.09 | 174.31 | 65.48 |
| α-MSH | 0 | 58.5 | 72.14 | 105.75 | 281.14 | 0 | 96.88 | 1157.87 | 77.41 | 0 | 106.1 | 62.93 | 0 |
| K(D)PT | 0 | 60.41 | 78.32 | 124.13 | 373.93 | 0 | 124 | 1039.39 | 87.48 | 0 | 77.74 | 71.69 | 0 |
| MMF | 0 | 62.31 | 90.45 | 100.77 | 337.89 | 0 | 90.56 | 745.12 | 80.11 | 0 | 88.47 | 61.12 | 0 |
| Dexamethasone | 0 | 50.19 | 69.18 | 98.48 | 249.8 | 0 | 88.47 | 586.12 | 84.69 | 0 | 67.18 | 64.23 | 0 | primary murine T-cells stimulated with PMA/Ionomycin, cytokine concentration [pg/ml]

| Substance | IL-13 | IL-1 | IL-22 | IL-2 | IL-5 | IL-21 | IL-6 | IL-10 | IL-27 | IFN-γ | TNF-α | IL-4 | IL-17 |
|---|---|---|---|---|---|---|---|---|---|---|---|---|---|
| PBS | 28.32 | 394.58 | 637.02 | 478.56 | 473.93 | 112.39 | 310.34 | 920.36 | 276.49 | 10860.7 | 162.21 | 142.94 | 307.43 |
| α-MSH | 0 | 217.32 | 143.37 | 163.19 | 215.44 | 0 | 174.22 | 1250.21 | 104.52 | 1458.12 | 77.76 | 91.65 | 29.47 |
| K(D)PT | 0 | 175.59 | 90.3 | 152.69 | 238.08 | 0 | 201.87 | 1133.29 | 126.71 | 2117.29 | 49.63 | 72.07 | 70.93 |
| MMF | 0 | 158.59 | 111.98 | 109.88 | 200.98 | 0 | 169.84 | 995.6 | 102.96 | 1808.99 | 50.14 | 64.89 | 67 |
| Dexamethasone | 0 | 160.95 | 97.01 | 97.41 | 198.45 | 0 | 144.26 | 899.74 | 94.12 | 1777.98 | 36.25 | 57.84 | 76.12 | primary murine T-cells stimulated with IFN-γ, cytokine concentration [pg/ml]

| Substance | IL-13 | IL-1 | IL-22 | IL-2 | IL-5 | IL-21 | IL-6 | IL-10 | IL-27 | IFN-γ | TNF-α | IL-4 | IL-17 |
|---|---|---|---|---|---|---|---|---|---|---|---|---|---|
| PBS | 0 | 159.07 | 75.55 | 163.26 | 452.71 | 41.32 | 266.16 | 867.48 | 282.91 | | 75.69 | 195.06 | 154.59 |
| α-MSH | 0 | 88.22 | 50.6 | 96.1 | 220.39 | 0 | 133.9 | 1117.07 | 104.04 | | 36.8 | 20.56 | 55.11 |
| K(D)PT | 0 | 93.77 | 48.13 | 98.22 | 271.81 | 0 | 144.97 | 1061 | 0 | | 34.84 | 85.32 | 88.84 |
| MMF | 0 | 100.02 | 55.98 | 79.63 | 254.61 | 0 | 111.95 | 936.45 | 40.8 | | 33.64 | 59.48 | 61.58 |
| Dexamethasone | 0 | 64.89 | 37.13 | 70.49 | 208.28 | 0 | 108.76 | 905.55 | 21.29 | | 32.32 | 61.11 | 52.48 | primary human T-cells stimulated with PBS, cytokine concentration [pg/ml]

| Substance | IL-12 | IFN-γ | IL-17 | IL-2 | IL-10 | IL-9 | IL-22 | IL-6 | IL-13 | IL-4 | IL-5 | IL-1 | TNF-a |
|---|---|---|---|---|---|---|---|---|---|---|---|---|---|
| PBS | 0 | 558.41 | 268.55 | 302.37 | 123.94 | 95.58 | 0 | 198.34 | 285.36 | 186.54 | 164.77 | 433.48 | 113.92 |
| α-MSH | 0 | 0 | 139.74 | 139.68 | 164.01 | 34.99 | 0 | 117.88 | 185.71 | 72.42 | 14.37 | 0 | 59.06 |
| K(D)PT | 0 | 0 | 127.21 | 0 | 159.09 | 0 | 0 | 109.89 | 172.66 | 0 | 0 | 147.97 | 65.47 |
| MMF | 0 | 0 | 71.42 | 39.68 | 79.26 | 28.13 | 0 | 94.62 | 79.09 | 0 | 0 | 0 | 53.91 |
| Dexamethasone | 0 | 0 | 69.45 | 0 | 45.66 | 13.05 | 0 | 80.63 | 55.12 | 0 | 0 | 0 | 41.45 | primary human T-cells stimulated with PMA/Ionomycin, cytokine concentration [pg/ml]

| Substance | IL-12 | IFN-γ | IL-17 | IL-2 | IL-10 | IL-9 | IL-22 | IL-6 | IL-13 | IL-4 | IL-5 | IL-1 | TNF-a |
|---|---|---|---|---|---|---|---|---|---|---|---|---|---|
| PBS | 0 | 20668.7 | 3370.25 | 10549.5 | 802.68 | 767.48 | 0 | 2981.92 | 1864.96 | 112.94 | 506.89 | 985.31 | 8233.81 |
| α-MSH | 0 | 10814.4 | 1660.92 | 2307.5 | 977.83 | 264.59 | 0 | 1241.17 | 1065.69 | 70.32 | 278.92 | 530.55 | 3346.46 |
| K(D)PT | 0 | 12070.4 | 1808.01 | 3486.84 | 877.54 | 332.07 | 0 | 1535.49 | 1158.74 | 41.83 | 379.39 | 594.38 | 3998.01 |
| MMF | 0 | 9491.25 | 1097.19 | 1498.52 | 814.79 | 339.89 | 0 | 1198.6 | 1072.09 | 29.49 | 309.88 | 505.05 | 3987.21 |
| Dexamethasone | 0 | 888.61 | 1134.18 | 2198.45 | 799.85 | 392.74 | 0 | 1078.6 | 1099.59 | 79.02 | 297.13 | 448.69 | 3264.56 |

TABLE 9-continued

Cytokine expression in murine and human cells following activation with PMA/Ionomycin and IFN-γ, respectively, and stimulation with the negative control (PBS) and α-MSH, K(D)PT, MMF and dexamethasone (concentration: $10^{-9}$M).

primary human T-cells stimulated with IFN-γ, cytokine concentration [pg/ml]

| | IL-12 | IFN-γ | IL-17 | IL-2 | IL-10 | IL-9 | IL-22 | IL-6 | IL-13 | IL-4 | IL-5 | IL-1 | TNF-α |
|---|---|---|---|---|---|---|---|---|---|---|---|---|---|
| PBS | 0 | 120.31 | 178.78 | 0 | 15.92 | 0 | 104.38 | 187.86 | 134.71 | 117.91 | 79.74 | 73.01 | |
| α-MSH | 0 | 0 | 0 | 43.9 | 5.27 | 0 | 64.54 | 0 | 60.49 | 0 | 0 | 18.85 | |
| K(D)PT | 0 | 0 | 0 | 33.21 | 9.51 | 0 | 58.47 | 0 | 0 | 0 | 0 | 0 | |
| MMF | 0 | 0 | 0 | 0 | 0 | 0 | 62.15 | 0 | 0 | 0 | 0 | 0 | |
| Dexamethasone | 0 | 0 | 0 | 0 | 0 | 0 | 56.47 | 0 | 0 | 0 | 0 | 0 | |

HaCaT stimulated with PBS, cytokine concentration [pg/ml]

| | IL-12 | IFN-γ | IL-17 | IL-2 | IL-10 | IL-9 | IL-22 | IL-6 | IL-13 | IL-4 | IL-5 | IL-1 | TNF-α |
|---|---|---|---|---|---|---|---|---|---|---|---|---|---|
| PBS | 0 | 391.65 | 45.41 | 233.68 | 32.84 | 18.84 | 0 | 182.52 | 1910.23 | 229.6 | 51.29 | 195.08 | 38.87 |
| α-MSH | 0 | 0 | 0 | 0 | 39.54 | 9.51 | 0 | 15.22 | 0 | 118.52 | 0 | 0 | 0 |
| K(D)PT | 0 | 99.65 | 0 | 0 | 31.43 | 5.27 | 0 | 78.34 | 0 | 144.86 | 0 | 65.11 | 9.34 |
| MMF | 0 | 0 | 0 | 0 | 33.26 | 0 | 0 | 39.58 | 0 | 120.89 | 0 | 0 | 0 |
| Dexamethasone | 0 | 12.98 | 0 | 0 | 30.89 | 0 | 0 | 44.79 | 0 | 133.98 | 0 | 0 | 0 |

HaCaT stimulated with PMA/Ionomycin, cytokine concentration [pg/ml]

| | IL-12 | IFN-γ | IL-17 | IL-2 | IL-10 | IL-9 | IL-22 | IL-6 | IL-13 | IL-4 | IL-5 | IL-1 | TNF-α |
|---|---|---|---|---|---|---|---|---|---|---|---|---|---|
| PBS | 0 | 109.28 | 101.48 | 172.29 | 78.59 | 14.7 | 0 | 422.8 | 1879.36 | 235.96 | 71.04 | 162.79 | 83.03 |
| α-MSH | 0 | 0 | 0 | 0 | 93.2 | 0 | 0 | 179.03 | 0 | 113.12 | 0 | 0 | 0 |
| K(D)PT | 0 | 0 | 0 | 0 | 118.77 | 0 | 0 | 282.85 | 0 | 129.6 | 0 | 0 | 0 |
| MMF | 0 | 0 | 0 | 0 | 66.23 | 0 | 0 | 116.51 | 0 | 98.71 | 0 | 0 | 0 |
| Dexamethasone | 0 | 0 | 0 | 0 | 54.10 | 0 | 0 | 124.98 | 0 | 91.48 | 0 | 0 | 0 |

HaCaT stimulated with IFN-γ, cytokine concentration [pg/ml]

| | IL-12 | IFN-γ | IL-17 | IL-2 | IL-10 | IL-9 | IL-22 | IL-6 | IL-13 | IL-4 | IL-5 | IL-1 | TNF-α |
|---|---|---|---|---|---|---|---|---|---|---|---|---|---|
| PBS | 0 | 196.73 | 263.44 | 43.65 | 18.37 | 0 | 386.69 | 1987.25 | 176.06 | 115.61 | 177.43 | 148.14 | |
| α-MSH | 0 | 95.44 | 0 | 0 | 0 | 0 | 202.37 | 0 | 0 | 0 | 0 | 45.91 | |
| K(D)PT | 0 | 112.82 | 131.59 | 0 | 0 | 0 | 238.12 | 0 | 52.4 | 0 | 0 | 50.44 | |
| MMF | 0 | 58.48 | 0 | 0 | 0 | 0 | 239.05 | 0 | 33.01 | 0 | 0 | 0 | |
| Dexamethasone | 0 | 69.14 | 0 | 0 | 0 | 0 | 204.99 | 0 | 39.78 | 0 | 0 | 0 | |

Assays in which the cytokine concentration in the supernatant was below the limit of detection are marked gray. Gray hatched cells indicated assays in which cytokine quantification is compromised due to the stimulant.

B. Vasculitis Model in Mice

C57BL/6 mice receive an intradermal injection of LPS. On the following day vasculitis is induced by intradermal injection of TNF-α. In addition Evan's blue is injected. 24 hours following the injection of TNF-α mice are scarified. Ear thickness is measured and the degree of vasculitis is assessed by counting petechiae. The content of Evan's blue in the ear tissue is a marker for vascular permeability. Ears are analyzed by histology, FACS and RT-qPCR. Treatment with example 13 (s.c.) resulted in a reduction of ear thickness and a reduced number of petechiae. In histology a reduced inflammatory infiltrate was seen.

C. Imiquimod-Induced Psoriasis in Mice

Psoriasis in Balb/c mice is induced by daily application of topical Imiquimod for 8 days. Animal are treated with the test items (topical or systemically). On day 9 the skin phenotype is characterized using a clinical score system (0=normal mouse skin; 1=mild reddening; 2=erythema; 3=erythema, swelling; 4=erythema, swelling, scaling; 5=erythema, swelling, scaling, (bloody) lesions). Skin is analyzed histologically. Lymph nodes are analyzed by flow cytometry and RT-qPCR. mRNA expression in lesional skin is analyzed by RT-qPCR. Cytokine concentrations in the serum are assessed using the Luminex technology.

Treatment with example 13 (i.v.) resulted in a decreased size of the rete ridges as compared to vehicle control. The clinical score was reduced. mRNA expression of IL-17, IFN-γ, IL-23, IL-36 and IL-22 in lesional skin was reduced. Concentrations of TNF-α and IL-17 in the serum of treated mice were reduced.

Treatment with Examples 14, 15, 16 and 17 (i.v.) resulted in a reduced clinical score and reduced epidermal thickness. Concentrations of TNF-α and IL-17 in the serum of treated mice were reduced. mRNA expression of IFN-γ and IL-36 in lesional skin was reduced compared to vehicle control.

D. DSS-Induced Colitis in Mice

Colitis is induced by treatment of C57BL/6 mice with 2.5% dextran sulfate (DSS) in the drinking water for 7 days. Mice are treated with the test item. Weight is monitored daily. At day 8 mice are scarified. A haemocult test is performed. The size of the colon is measured. Colitis is determined using a scoring system in H&E stains. mRNA expression in colon samples is analyzed by RT-qPCR.

Treatment with example 13 (i.p.) resulted in a decreased weight loss compared to vehicle control. Colon size was partly normalized. An amelioration of the disease was observed in histology. Compared to vehicle control a reduced mRNA expression of LY-6G, MPO, IFN-γ, IL-6 and TNF-α was observed.

E. Skin Penetration Studies

Skin penetration studies are performed with excised human skin. Tissue samples are washed with saline postoperatively and the subcutaneous fat layer is removed. Punch biopsies (20 mm diameter, 3.14 cm$^2$) are taken and stored at −20° C. At the beginning of the penetration study the full thickness skin sample is thawed and dried with a swab. Penetration studies are performed applying Franz diffusion cells. Cream base containing the tripeptide compound is applied on the skin and distributed equally. The skin sample on gaze is placed on the diffusion cell which is tempered at 32° C. before. After 30, 100 and 300 min, respectively, remaining formulation is removed with a swab. After removal from the diffusion cell three punch biopsies (6 mm diameter) are taken. Horizontal sections are prepared from which the tripeptide compound is extracted. Peptide content in all extracts and the acceptor medium is analyzed with HPLC-MS.

F. Aqueous Stability

An aqueous solution of the tripeptide compound (1500 µl) with or without 0.02% sodium azide ($c_{peptide}$=160 µg/ml) is incubated at 32° C. and 8° C., respectively. Samples are taken at 0, 30, 100, 300 and 1000 minutes. 100 sample is diluted with 1900 µl methanol containing an internal standard and analyzed with HPLC-MS. All analyses are performed in triplicate.

No degradation was observed for Examples 3, 8 and 9 even after 1000 minutes.

G. Stability in the Presence of Homogenized Human Skin

Human skin samples (ear skin, umbilical skin and juvenile foreskin) are combined and frozen in liquid nitrogen and homogenized. The resulting human skin homogenate is transferred portionwise (50-70 mg) to Protein LoBind Tubes (2 ml) and stored at −32° C. until use. At the beginning of the stability study the human skin homogenate is thawed. An aqueous solution of the tripeptide compound (1500 µl) with or without 0.02% sodium azide ($c_{peptide}$=160 µg/ml) is added and the mixture is incubated at 32° C. Samples were taken at 0, 30, 100, 300 and 1000 minutes. 100 µl sample are diluted with 1900 µl methanol containing an internal standard and analyzed with HPLC-MS. All analyses are performed in triplicate.

After 30 and 100 minutes, respectively, the test solution contained still 94-95% of the starting concentration of Example 8. A decrease to 77-80% (300 min) and 40% (azide free) and 47% (with sodium azide), respectively, after 1000 min was observed.

The amount of Example 9 in the solution decreased to 58% (azide free) and 63% (with sodium azide), respectively, after 300 minutes.

No degradation was observed for Example 3. All samples at all time points contained 80-90% of the starting concentration.

Examples of Pharmaceutical Compositions

Composition for Example 3:

| Cream | |
|---|---|
| Example 3 | 1.00 |
| Cetostearyl alcohol | 7.00 |
| Macrogol-6-cetostearyl ether | 1.50 |
| Macrogol-25-cetostearyl ether | 1.50 |
| Liquid paraffin | 12.00 |
| Propylene glycol | 8.00 |
| Methylparaben | 0.15 |
| Ethylparaben | 0.08 |
| Butylhydroxytoluene | 0.04 |
| Disodium edetate | 0.05 |
| Water | 68.68 |

Composition for Example 8:

| Gel | |
|---|---|
| Example 8 | 0.50 |
| Ethanol | 15.00 |
| Polyoxyl 40 Hydrogenated Castor Oil | 1.00 |
| Butylhydroxytoluene | 0.04 |
| Disodium edetate | 0.05 |
| Carbomer | 0.50 |
| Triethanolamine | 0.70 |
| Water | 82.21 |

Composition for Example 3:

As a specific embodiment of an oral composition of a compound of the present invention, 21 mg of Example 3 is formulated with sufficient finely divided lactose to provide a total amount of 580 to 590 mg to fill a size 0 hard gelatin capsule.

Composition for Example 9:

As another specific embodiment of an oral composition of a compound of the present invention, 17 mg of Example 9 is formulated with sufficient finely divided lactose to provide a total amount of 580 to 590 mg to fill a size 0 hard gelatin capsule.

The invention claimed is:

1. A tripeptide compound selected from the group consisting of: H-(L)-Lys-(D)-Pro-N$^\alpha$-methyl-(L)-Thr-OH, N$^\alpha$,N$^\alpha$-dimethyl-(L)-Lys-(D)-Pro-N$^\alpha$-methyl-(L)-Thr-OH, N$^\alpha$,N$^\alpha$-dimethyl-(L)-Lys-(D)-Pro-N$^\alpha$-methyl-(L)-Thr-NH$_2$, N$^\alpha$,N$^\alpha$-dimethyl-(L)-Lys-(D)-Pro-N$^\alpha$-methyl-(L)-Val-OH, a solvate of any thereof a hydrate of any thereof, and a pharmaceutically acceptable salt of any thereof, wherein the tripeptide compound is anti-inflammatory.

2. A method of therapeutic and/or prophylactic treatment of disease, comprising: administering the tripeptide compound according to claim 1.

3. The method of claim 2, wherein the disease is selected from the group consisting of: acute pain, chronic pain, pruritus, hyponatremia, edema, ileus, tussis, glaucoma, and an inflammatory disease, wherein the inflammatory disease is an acute inflammatory disease or a chronic inflammatory disease.

4. The method of claim 3, wherein the inflammatory disease is selected from the group consisting of: cardiovascular inflammation, neurological inflammation, skeletal inflammation, skin inflammation, muscular inflammation, gastrointestinal inflammation, ocular inflammation, otic inflammation, inflammation due to insect bites, inflammation due to wound healing, atherosclerosis, ischemia, restenosis, vasculitis, asthma, Sjogren's syndrome, pulmonary inflammation, chronic airway inflammation, chronic obstructive pulmonary disease (COPD), allergy, psoriasis, psoriatic arthritis, eczema, scleroderma, atopic dermatitis, systemic lupus erythematosus, arthritis, synovitis, osteomyelitis, rheumatoid arthritis, osteoarthritis, ankylosing spondylitis; septicemia, septic shock, diabetes, glucose intolerance, insulin resistance, obesity, colitis, ulcerative colitis, Crohn's disease, IBD, IBS, inflammatory diseases and conditions due to tumor proliferation, inflammatory diseases and conditions due to tumor metastasis, and inflammatory diseases and conditions due to transplantation rejection.

5. The method of claim 3, wherein the inflammatory disease is selected from the group consisting of: sepsis, an inflammatory disease of the joints, vulvovaginitis, an inflammatory disease of the brain, an inflammatory disease of the skin, an inflammatory disease of the hair follicle, an inflammatory disease of the urogenital tract, an inflammatory disease of the eyes, sinusitis, tenosynovitis, bursitis, tendonitis, lateral epicondylitis, adhesive capsulitis, autoimmune inflammation, contact dermatitis, atopic eczema, alopecia areata, scleroderma, a fibrotic disease, urticaria, lichen planus, lymphoma, and a disease characterized by mast cell involvements.

6. A medicament comprising at least one tripeptide compound as claimed in claim 1.

7. The method of claim 3, wherein the inflammatory disease is an inflammatory disease of the gastrointestinal tract.

8. The method of claim 7, wherein the inflammatory disease of the gastrointestinal tract is an inflammatory bowel disease.

9. The method of claim 8, wherein the inflammatory bowel disease is selected from the group consisting of: Crohn's disease and colitis ulcerosa.

10. The method of claim 7, wherein the inflammatory disease of the gastrointestinal tract is selected from the group consisting of: inflammation of the gall bladder, inflammatory pseudopolyps, colitis cystica profunda, pneumatosis cystoides intestinales, pancreatitis, and appendicitis.

\* \* \* \* \*